United States Patent
Colandrea et al.

(10) Patent No.: US 8,471,024 B2
(45) Date of Patent: Jun. 25, 2013

(54) TETRAHYDROFUROPYRIDONES

(75) Inventors: Vincent J. Colandrea, North Brunswick, NJ (US); Jeffrey J. Hale, Westfield, NJ (US); Joshua G. McCoy, Westfield, NJ (US)

(73) Assignee: Merck Sharp & Dohme, Corp., Rahway, NJ (US)

( * ) Notice: Subject to any disclaimer, the term of this patent is extended or adjusted under 35 U.S.C. 154(b) by 240 days.

(21) Appl. No.: 12/919,156

(22) PCT Filed: Feb. 11, 2009

(86) PCT No.: PCT/US2009/033713
§ 371 (c)(1),
(2), (4) Date: Aug. 24, 2010

(87) PCT Pub. No.: WO2009/108496
PCT Pub. Date: Sep. 3, 2009

(65) Prior Publication Data
US 2010/0331358 A1    Dec. 30, 2010

Related U.S. Application Data

(60) Provisional application No. 61/066,979, filed on Feb. 25, 2008.

(51) Int. Cl.
*A61K 31/4355* (2006.01)
*C07D 491/048* (2006.01)

(52) U.S. Cl.
USPC .......................... 546/115; 514/302

(58) Field of Classification Search
USPC .......................... 546/115; 514/302
See application file for complete search history.

(56) References Cited

U.S. PATENT DOCUMENTS

2003/0176317 A1   9/2003   Guenzler-Pukall et al.
2007/0213335 A1   9/2007   Fitch

OTHER PUBLICATIONS

"Anemia: Prevention, Mayo Clinic" online "http://www.mayoclinic.com/health/anemia/DS00321/DSECTION=prevention Sep. 4, 2012" accessed Sep. 4, 2012.*
West, Anthony R., Solid State Chemistry and its Applications, Wiley, New York, 1988, pp. 358 & 365.*

* cited by examiner

*Primary Examiner* — David K O Dell
(74) *Attorney, Agent, or Firm* — Patricia A. Shatynski; Valerie J. Camara

(57) ABSTRACT

The present invention relates to Tetrahydrofuropyridones compounds useful as HIF prolyl hydroxylase inhibitors to treat anemia and like conditions.

14 Claims, No Drawings

TETRAHYDROFUROPYRIDONES

CROSS REFERENCE TO RELATED APPLICATIONS

This application is a U.S. National Phase application under 35 U.S.C. §371 of PCT Application No. PCT/US2009/033713, filed Feb. 11, 2009 which claims priority under 35 U.S.C. §119(e) from U.S. Provisional Application Ser. No. 61/066,979, filed Feb. 25, 2008.

BACKGROUND OF THE INVENTION

The insufficient delivery of oxygen to cells and tissues is associated with anemia, which is defined as a deficiency in the blood's oxygen-carrying capacity, and ischemia, in which restrictions in blood supply are caused by a constriction or blockage of blood vessels. Anemia can be caused by the loss of red blood cells (hemorrhage), excessive red blood cell destruction (hemolysis) or deficiencies in erythropoiesis (production of red blood cells from precursors found in the bone marrow). The symptoms of anemia can include weakness, dizziness, fatigue, pallor, impairment of cognitive function and a general reduction in quality of life. Chronic and/or severe anemia can lead to the exacerbation of myocardial, cerebral or peripheral ischemia and to heart failure. Ischemia is defined as an absolute or relative shortage of oxygen to a tissue or organ and can result from disorders such as atherosclerosis, diabetes, thromboembolisms, hypotension, etc. The heart, brain and kidney are especially sensitive to ischemic stress caused by low blood supply.

The primary pharmacological treatment for anemia is administration of some variant of recombinant human erythropoietin (EPO). For anemias associated with kidney disease, chemotherapy-induced anemia, anemia from HIV-therapy or anemia due to blood loss, recombinant EPO is administered to enhance the supply of the hormone, correct the shortage of red blood cells and increase the blood's oxygen-carrying capacity. EPO replacement is not always sufficient to stimulate optimal erythropoiesis (e.g., in patients with iron processing deficiencies) and has associated risks.

Hypoxia-inducible factor (HIF) has been identified as a primary regulator of the cellular response to low oxygen. HIF is a heterodimeric gene transcription factor consisting of a highly regulated α-subunit (HIF-α) and a constitutively expressed β-subunit (HIF-β, also known as ARNT, or aryl hydrocarbon receptor nuclear transporter). HIF target genes are reported to be associated with various aspects of erythropoiesis (e.g., erythropoietin (EPO) and EPO receptor), glycolysis and angiogenesis (e.g., vascular endothelial growth factor (VEGF)). Genes for proteins involved in iron absorption, transport and utilization as well as heme synthesis are also targets of HIF.

Under normal oxygenation, HIF-α is a substrate in a reaction with molecular oxygen, which is catalyzed by a family of iron(II)-, 2-ketoglutarate- and ascorbate-dependent dioxygenase enzymes called PHD-1 (EGLN2, or egg laying abnormal 9 homolog 2, PHD2 (EGLN1), and PHD3 (EGLN3). Proline residues of HIF-α are hydroxylated (e.g., Pro-402 and Pro-564 of HIF-1α) and the resulting product is a target of the tumor suppressor protein von-Hippel Lindau, a component of an E3 ubiquitin ligase multiprotein complex involved in protein ubiquitination. Under low oxygenation, the HIF-α hydroxylation reaction is less efficient and HIF-α is available to dimerize with HIF-β HIF dimers are translocated to the cell nucleus where they bind to a hypoxia-responsive enhancer element of HIF target genes.

Cellular levels of HIF are known to increase under conditions of hypoxia and after exposure to hypoxia mimetic agents. The latter includes, but is not limited to, specific metal ions (e.g., cobalt, nickel, manganese), iron chelators (e.g., desferrioxamine) and analogs of 2-ketoglurate (e.g., N-oxalyl glycine). The compounds of the present invention inhibit the HIT prolyl hydroxylases (PHD-1, PHD-2, PHD-3) and can also serve to modulate HIF levels. These compounds therefore have utility for the treatment and/or prevention of disorders or conditions where HIF modulation is desirable, such as anemia and ischemia. As an alternative to recombinant erythropoietin therapy, the compounds of the present invention provide a simpler and broader method for the management of anemia.

SUMMARY OF THE INVENTION

The present invention concerns compounds of formula I,

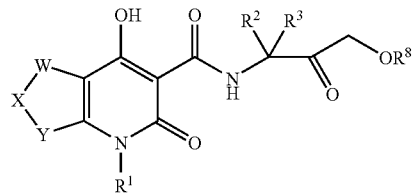

which inhibit HIF prolyl hydroxylase, their use for enhancing endogenous production of erythropoietin, and for treating conditions associated with reduced endogenous production of erythropoietin such as anemia and like conditions, as well as pharmaceutical compositions comprising such a compound and a pharmaceutical carrier.

DETAILED DESCRIPTION OF THE INVENTION

The present invention provides compounds of formula I and pharmaceutically acceptable salts and solvates thereof:

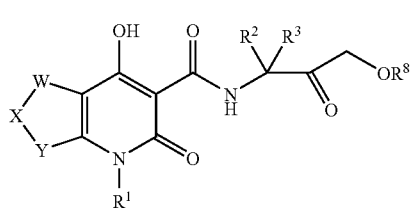

wherein
one of X, Y, or W is O and the other two moieties are —$CR^4R^5$ and —$CR^6R^7$;
$R^8$ is selected from hydrogen, $C_{1-6}$ alkyl, optionally substituted with a hydroxy, —SH, —$NH_2$ or —$CO_2H$, and $C_{3-6}$ cycloalkyl optionally substituted with a hydroxy, —SH, —$NH_2$ or —$CO_2H$;
n is 0, 1, or 2;
$R^1$ is selected from
—$C_{1-10}$ alkyl,
—$C_{2-10}$ alkenyl,
—$C_{5-10}$ cycloalkenyl,
—$C_{2-10}$ alkynyl,
—$C_{0-10}$ alkylaryl,
—$C_{0-10}$ alkylheterocyclyl,
—$C_{0-10}$ alkyl-$C_{0-10}$cycloalkyl, and perfluoro$C_{1-6}$alkyl;

wherein in $R^1$ said alkyl, alkenyl, alkynyl, cycloalkenyl, aryl, heterocycloalkyl, heterocyclyl, and cycloalkyl are each optionally substituted with one or more $R^9$ substituents;

$R^2$ and $R^3$ are independently selected from hydrogen, phenyl, heterocyclyl, and —$C_{1-10}$ alkyl, wherein $C_{1-10}$ alkyl is unsubstituted or substituted with one or more fluorine atoms, and phenyl is unsubstituted or substituted with or more substituents selected from fluoro, chloro, hydroxyl, $C_{1-10}$ alkyl, and —$OC_{1-10}$ alkyl;

$R^4$, $R^5$, $R^6$, and $R^7$ are independently selected from hydrogen, cyano, oxo, —$C_1$-$C_{10}$ alkyl, —$C_{2-10}$ alkenyl, —$C_{3-10}$ cycloalkyl, —($C_{1-10}$ alkyl)aryl, ($C_{0-10}$ alkyl)heterocyclyl, —$C_{5-10}$ cycloalkenyl, —$C_{2-10}$ alkynyl, —$SO_n(C_{1-10}$ alkyl) and —$SO_n$aryl wherein said alkyl, alkenyl, alkynyl, cycloalkyl, cycloalkenyl, aryl, and heterocyclyl are optionally substituted by one or more substituents $R^9$, and optionally one set of substituents, $R^4$ and $R^5$, or $R^6$ and $R^7$, are linked together to form a ring of 5 to 8 atoms optionally substituted with one or more substituents $R^9$, where said ring is partially or fully unsaturated having 0, 1 or 2 heteroatoms independently selected from —$NR^6$—, —O— and —$S(O)_n$—;

$R^9$ is selected from halogen, hydroxy, oxo, cyano, aryl, heterocyclyl, —$C_{1-6}$ alkyl, $O(C=O)_{0-1}C_{1-6}$ alkyl, —$C_{1-6}$ alkoxy, —$O_{(0-1)}(C_{1-10})$perfluoroalkyl, aryloxy, heterocyclyloxy, —$CO_2R^a$, —$NR^bR^c$, —$CONR^bR^c$, —$OCO_2R^a$, —$OCONR^bR^c$, —$NR^dCO_2R^a$, $NR^dCONR^bR^c$, —$SC_{0-6}$ alkyl and —$S(O)_nR^d$, wherein said aryl, heterocyclyl, alkoxy, aryloxy, heterocyclyloxy are optionally substituted by one or more substituents $R^{10}$;

$R^{10}$ is selected from hydroxy, aryl, heterocyclyl, halogen, —$C_{1-6}$ alkyl, $C_{1-6}$ alkoxy, halogen, $CO_2H$, cyano, $O(C=O)_{0-1}C_{1-6}$ alkyl, $NO_2$, trifluoromethoxy, trifluoroethoxy, —$O_{(0-1)}(C_{1-10})$perfluoroalkyl, $C_{0-10}$ alkylaminocarbonylamino, $C_{0-10}$ alkyloxycarbonylamino$C_{0-10}$ alkyl, $C_{0-10}$ alkylcarbonylamino$C_{0-10}$alkyl, $C_{0-10}$ alkylaminosulfonylamino$C_{0-10}$ alkyl, $C_{0-10}$ alkylsulfonylamino$C_{0-10}$ alkyl, $C_{0-10}$ alkylsulfonyl, $C_{0-10}$ alkylaminosulfonyl, $C_{0-10}$ alkylaminocarbonyl, —$(C=O)N(C_{0-6}$ alkyl)$_2$, —$S(C_{0-6}$ alkyl), and $NH_2$;

$R^a$ is chosen from hydrogen; —$C_{1-10}$ alkyl, —($C_{1-6}$ alkyl)$C_{3-8}$ cycloalkyl; and —($C_{1-6}$ alkyl)phenyl; and $R^b$, $R^c$, and $R^d$ are each independently chosen from hydrogen, —$C_{1-10}$ alkyl, —$C_{3-10}$ cycloalkyl, aryl, and heterocyclyl, wherein said alkyl, cycloalkyl, aryl and heterocyclyl are optionally substituted by one or more subtstituents $R^{10}$.

Illustrative but nonlimiting examples of compounds of the invention are the following:

N-{[(1-(1,3-benzothiazol-2-ylmethyl)-4-hydroxy-2-oxo-1,2,5,7-tetrahydrofuro[3,4-b]pyridin-3-yl]carbonyl)glycine;

N-({4-hydroxy-2-oxo-[4]1-[4-(trifluoromethyl)benzyl]-1,2,5,7-tetrahydrofuro[3,4-b]pyridin-3-yl}carbonyl)glycine;

N-[(4-hydroxy-2-oxo-1-{[6-(trifluoromethyl)pyridine-3-yl]methyl}-1,2,5,7-tetrahydrofuro[3,4-b]pyridin-3-yl)carbonyl]glycine;

N-{[4-hydroxy-2-oxo-1-(pyridazin-3-ylmethyl)-1,2,5,7-tetrahydrofuro[3,4-b]pyridin-3-yl]carbonyl}glycine;

N-({4-hydroxy-2-oxo-1-[(5-phenyl-1,2,4-oxadiazol-3-yl)methyl]-1,2,5,7-tetrahydrofuro[3,4-b]pyridin-3-yl}carbonyl)glycine;

N-({4-hydroxy-2-oxo-[4]1-[4-(trifluoromethoxy)benzyl]-1,2,5,7-tetrahydrofuro[3,4-b]pyridin-3-yl}carbonyl)glycine;

N-({4-hydroxy-1-[(5-methylpyrazin-2-yl)methyl-2-oxo-1,2,5,7-tetrahydrofuro[3,4-b]pyridin-3-yl}carbonyl)glycine;

N-{[4-hydroxy-1-(4-isopropoxybenzyl)-2-oxo-1,2,5,7-tetrahydrofuro[3,4-b]pyridin-3-yl]carbonyl}glycine;

N-({1-[(6-chloropyridin-3-yl)methyl]-4-hydroxy-2-oxo-1,2,5,7-tetrahydrofuro[3,4-b]pyridin-3-yl}carbonyl)glycine;

N-{[1-(4-bromobenzyl)-4-hydroxy-2-oxo-1,2,5,7-tetrahydrofuro[3,4-b]pyridin-3-yl]carbonyl}glycine;

N-{[1-(2,3-dihydro-1H-inden-2-ylmethyl)-4-hydroxy-2-oxo-1,2,5,7-tetrahydrofuro[3,4-b]pyridin-3-yl]carbonyl}glycine;

N-({1-[(5-chloropyrazin-2-yl)methyl]-4-hydroxy-2-oxo-1,2,5,7-tetrahydrofuro[3,4-b]pyridin-3-yl}carbonyl)glycine;

N-({4-hydroxy-5-methyl-2-oxo-[4]1-[4-(trifluoromethyl)benzyl]-1,2,5,7-tetrahydrofuro[3,4-b]pyridin-3-yl}carbonyl)glycine;

N-[(4-hydroxy-5-methyl-2-oxo-1-{[6-(trifluoromethyl)pyridine-3-yl]methyl}-1,2,5,7-tetrahydrofuro[3,4-b]pyridin-3-yl}carbonyl)glycine;

N-{[1-(4-bromo-2-fluorobenzyl)-4-hydroxy-2-oxo-1,2,5,7-tetrahydrofuro[3,4-b]pyridin-3-yl]carbonyl}glycine;

N-{[1-(3-chlorobenzyl)-4-hydroxy-2-oxo-1,2,5,7-tetrahydrofuro[3,4-b]pyridin-3-yl]carbonyl}glycine;

N-{[1-(4-difluoromethoxybenzyl)-4-hydroxy-2-oxo-1,2,5,7-tetrahydrofuro[3,4-b]pyridin-3-yl]carbonyl}glycine;

N-({4-hydroxy-2-oxo-1-[3-(1H-pyrazole-1-yl)benzyl]-1,2,5,7-tetrahydrofuro[3,4-b]pyridin-3-yl}carbonyl)glycine;

N-[(4-hydroxy-2-oxo-1-{[6-(2,2,2-trifluoroethoxy)pyridin-3-yl]methyl}-1,2,5,7-tetrahydrofuro[3,4-b]pyridin-3-yl)carbonyl]glycine;

N-[(4-hydroxy-1-{[1-(2-methylphenyl)-1H-pyrazol-3-yl]methyl}-2-oxo-1,2,5,7-tetrahydrofuro[3,4-b]pyridin-3-yl)carbonyl]glycine;

N-({4-hydroxy-1-[(5-methyl-2-phenyl-2H-1,2,3-triazol-4-yl)methyl]-2-oxo-1,2,5,7-tetrahydrofuro[3,4-b]pyridin-3-yl}carbonyl)glycine;

N-[(1-{[1-(4-fluorophenyl)-1H-pyrazol-3-yl]methyl-4-hydroxy-2-oxo-1,2,5,7-tetrahydrofuro[3,4-b]pyridin-3-yl)carbonyl]glycine;

N-({4-hydroxy-2-oxo-1-[4-(1,3-thiazol-2-yl)benzyl]-1,2,5,7-tetrahydrofuro[3,4-b]pyridin-3-yl}carbonyl)glycine;

N-({4-hydroxy-2-oxo-1-[4-(2,2,2-trifluoroethoxy)benzyl]-1,2,5,7-tetrahydrofuro[3,4-b]pyridin-3-yl}carbonyl)glycine;

N-{[(1-(1,3-benzothiazol-2-ylmethyl)-4-hydroxy-7,7-dimethyl-2-oxo-1,2,5,7-tetrahydrofuro[3,4-b]pyridin-3-yl]carbonyl)glycine;

N-[(1-{[4-(2,4-dichlorophenyl)-1,3-thiazol-2-yl]methyl)-4-hydroxy-2-oxo-1,2,5,7-tetrahydrofuro[3,4-b]pyridin-3-yl)carbonyl]glycine;

N-[(1-{[4-(2-chlorophenyl)-1,3-thiazol-2-yl]methyl)-4-hydroxy-2-oxo-1,2,5,7-tetrahydrofuro[3,4-b]pyridin-3-yl)carbonyl]glycine;

N-({1-[2'-chlorobiphenyl)methyl]-4-hyrdoxy-2-oxo-1,2,5,7-tetrahydrofuro[3,4-b]pyridin-3-yl}carbonyl)glycine;

N-[(1-{[6-(2-chlorophenyl)pyridine-3-yl]methyl}-4-hyrdoxy-2-oxo-1,2,5,7-tetrahydrofuro[3,4-b]pyridin-3-yl}carbonyl)glycine;

N-({1-[4'-chlorophenyl)methyl]-4-hyrdoxy-2-oxo-1,2,5,7-tetrahydrofuro[3,4-b]pyridin-3-yl}carbonyl)glycine;

N-({1-[4'-fluorophenyl)methyl]-4-hyrdoxy-2-oxo-1,2,5,7-tetrahydrofuro[3,4-b]pyridin-3-yl}carbonyl)glycine;

N-[(4-hydroxy-2-oxo-1-{[2'-(1H-pyrazol-yl)biphenyl-4-yl]methyl}-1,2,5,7-tetrahydrofuro[3,4-b]pyridin-3-yl}carbonyl)glycine;

N-[(4-hydroxy-2-oxo-1-{[2'-(trifluoromethyl)biphenyl-4-yl]methyl}-1,2,5,7-tetrahydrofuro[3,4-b]pyridin-3-yl}carbonyl)glycine;
N-[(4-hydroxy-1-{[2'-(2,2,2-trifluoroethoxy)biphenyl-4-yl]methyl}-2-oxo-1,2,5,7-tetrahydrofuro[3,4-b]pyridin-3-yl}carbonyl)glycine;
N-({1-[2',4'-dichlorobiphenyl-4-yl)methyl]-4-hydroxy-2-oxo-1,2,5,7-tetrahydrofuro[3,4-b]pyridin-3-yl}carbonyl)glycine;
N-[(4-hydroxy-1-{[2'-(methoxycarbonyl)biphenyl-4-yl]methyl}-2-oxo-1,2,5,7-tetrahydrofuro[3,4-b]pyridin-3-yl}carbonyl)glycine;
N-({1-[2'-chloro-4'-fluorobiphenyl-4-yl)methyl]-4-hydroxy-2-oxo-1,2,5,7-tetrahydrofuro[3,4-b]pyridin-3-yl}carbonyl)glycine;
N-({1-[2'-chloro-3-fluorobiphenyl-4-yl)methyl]-4-hydroxy-2-oxo-1,2,5,7-tetrahydrofuro[3,4-b]pyridin-3-yl}carbonyl)glycine;
N-({1-[2'-chloro-3 ,4'-difluorobiphenyl-4-yl)methyl]-4-hydroxy-2-oxo-1,2,5,7-tetrahydrofuro[3,4-b]pyridin-3-yl}carbonyl)glycine;
N-{[1-({2'-(diethylamino)carbonyl]-3-fluorobiphenyl-4-yl}methyl)-4-hydroxy-2-oxo-1,2,5,7-tetrahydrofuro[3,4-b]pyridin-3-yl}carbonyl)glycine;
N-({4-hyrdoxy-2-oxo-1-[(6-phenylpyridin-3-yl)methyl]-1,2,5,7-tetrahydrofuro[3,4-b]pyridin-3-y1}carbonyl)glycine;
N-[(1-{[6-(3,5-dichlorophenyl)pyridin-3-yl]methyl}-4-hyrdoxy-2-oxo-1,2,5,7-tetrahydrofuro[3,4-b]pyridin-3-yl)carbonyl]glycine;
N-[(4-hyrdoxy-1-{[6-(1-methyl-1H-pyrazol-4-yl)pyridin-3-yl]methyl}-2-oxo-1,2,5,7-tetrahydrofuro[3,4-b]pyridin-3-yl)carbonyl]glycine;
N-[(1-{[6-(2,4-difluorophenyl)pyridin-3-yl]methyl}-4-hyrdoxy-2-oxo-1,2,5,7-tetrahydrofuro[3,4-b]pyridin-3-yl)carbonyl]glycine;
N-[(1-{[6-(2,5-difluorophenyl)pyridin-3-yl]methyl}-4-hyrdoxy-2-oxo-1,2,5,7-tetrahydrofuro[3,4-b]pyridin-3-yl)carbonyl]glycine;
N-{[4-hyrdoxy-2-oxo-1-({6-[2,2,2-trifluoroethoxy)phenyl]pyridin-3-yl}methyl]-1,2,5,7-tetrahydrofuro[3,4-b]pyridin-3-yl]carbonyl}glycine;
N-{[4-hyrdoxy-2-oxo-1-({6-[2-(trifluoromethyl)phenyl]pyridin-3-yl}methyl)-1,2,5,7-tetrahydrofuro[3,4-b]pyridin-3-yl]carbonyl}glycine;
N-{[4-hyrdoxy-2-oxo-1-({6-[2-(trifluoromethoxy)phenyl]pyridin-3-yl}methyl)-1,2,5,7-tetrahydrofuro[3,4-b]pyridin-3-yl]carbonyl}glycine;
N-[(1-{[6-(2-fluorophenyl)pyridin-3-yl]methyl}-4-hyrdoxy-2-oxo-1,2,5,7-tetrahydrofuro[3,4-b]pyridin-3-yl)carbonyl]glycine;
N-[(1-{[6-(2-chloro-4-fluorophenyl)pyridin-3-yl]methyl}-4-hyrdoxy-2-oxo-1,2,5,7-tetrahydrofuro[3,4-b]pyridin-3-yl)carbonyl]glycine;
N-[(1-{[5-(2,4-difluorophenyl)pyrazin-2-yl]methyl}-4-hyrdoxy-2-oxo-1,2,5,7-tetrahydrofuro[3,4-b]pyridin-3-yl)carbonyl]glycine;
N-[(1-{[5-(3,4-difluorophenyl)pyrazin-2-yl]methyl}-4-hyrdoxy-2-oxo-1,2,5,7-tetrahydrofuro[3,4-b]pyridin-3-yl)carbonyl]glycine;
N-[(1-{[5-(2-chlorophenyl)pyrazin-2-yl]methyl}-4-hyrdoxy-2-oxo-1,2,5,7-tetrahydrofuro[3,4-b]pyridin-3-yl)carbonyl]glycine;
N-[(1-{[5-(2-trifluoromethoxyphenyl)pyrazin-2-yl]methyl}-4-hyrdoxy-2-oxo-1,2,5,7-tetrahydrofuro[3,4-b]pyridin-3-yl)carbonyl]glycine, and pharmaceutically acceptable salts and solvates thereof.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

Unless otherwise specifically noted as only "unsubstituted" or only "substituted", or when substituents are enumerated, alkyl (either as a stand alone radical or as part of a radical such as alkoxy, alkylthio and aralkyl) groups are unsubstituted or substituted with 1to 3 substituents on each carbon atom, with halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S$(O)_{0-2}$—, ($C_0$-$C_6$ alkyl)S$(O)_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, —NH($C_1$-$C_6$ alkyl)NHC(O)—NH($C_1$-$C_6$ alkyl), NHC(O)O$C_1$-$C_6$ alkyl, —NH($C_1$-$C_6$ alkyl)NHSO$_2$($C_1$-$C_6$ alkyl), —($C_0$-$C_6$ alkyl)NHSO$_2$($C_1$-$C_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "$C_0$" as employed in expressions such as "$C_{0-6}$ alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

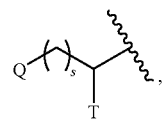

wherein s is an integer equal to zero, 1or 2, the structure is

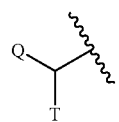

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, 2,3-dihydro-1H-indenyl, and biphenyl.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

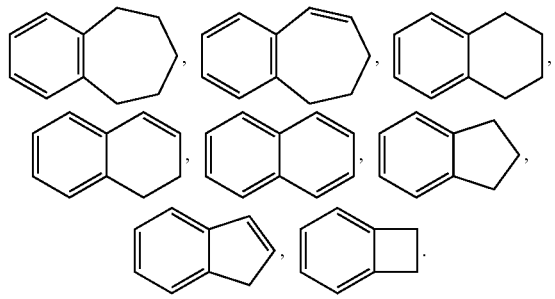

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Non limiting examples of heterocyclylic moieties include, but are not limited to, the following: azabenzimidazole, benzoimidazolyl, benzofuranyl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuranyl, isochromanyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofttranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, tetrahidroquinolinyl, 2,3-dihydrobenzofuranyl, 2,3-dihydrobenzo-1,4-dioxinyl, imidazo(2,1-b)(1,3)thiazole, and benzo-1,3-dioxolyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

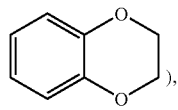), imidazo(2,1-b)(1,3)thiazole. (i.e.,

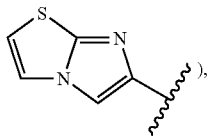 [SMILES: *c1cn2ccsc2n1]), and benzo-1,3-dioxolyl (i.e.,

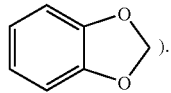).

In certain contexts herein,

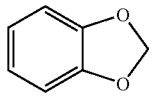

is alternatively referred to as phenyl having as a substituent methylenedioxy attached to two adjacent carbon atoms.

The terms "arylalkyl" and "alkylaryl" include an alkyl portion where alkyl is as defined above and include an aryl portion where aryl is as defined above. Examples of arylalkyl include, but are not limited to, benzyl, phenylethyl, phenylpropyl, naphthylmethyl, and naphthylethyl. Examples of alkylaryl include, but are not limited to, toluene, ethylbenzene, propylbenzene, methylpyridine, ethylpyridine, propylpyridine and butylpyridine.

Unless otherwise specifically noted as only "unsubstituted" or only "substituted", or when substituents are specifically enumerated, cycloalkyl, aryl (including phenyl) and heterocycle (including heteroaryl) groups are unsubstituted or substituted. As used herein, the terms "substituted $C_3$-$C_{10}$ cycloalkyl", "substituted aryl (including phenyl)" and "substituted heterocycle" are intended to include the cyclic group containing from 1 to 3 substituents in addition to the point of attachment to the rest of the compound. Preferably, the substituents are selected from the group which includes, but are not limited to, halo, $C_1$-$C_{20}$ alkyl, $CF_3$, $N(C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, aryl-S(O)$_{0-2}$—, ($C_0$-$C_6$ alkyl)S(O)$_{0-2}$($C_0$-$C_6$ alkyl)-, ($C_0$-$C_6$ alkyl) C(O)NH—, $H_2N$—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)$_2$NC(O)—($C_0$-$C_6$alkyl)O($C_1$-$C_6$ alkyl)-, ($C_0$-$C_6$ alkyl)C(O)$_{1-2}$ ($C_0$-$C_6$ alkyl)-, ($C_0$-$C_6$ alkyl)OC(O)NH—, aryl, aralkyl, heterocyclyl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

In one embodiment of the invention, $R_1$ is selected from —$C_{1-10}$ alkyl, —$C_{0-10}$ alkylaryl, —$C_{0-10}$ alkylheterocyclyl; —$C_{0-10}$ alkyl-$C_{3-10}$cycloalkyl, and perfluoro$C_{1-6}$alkyl.

In a subset of this embodiment, $R_1$ is selected from —$C_{0-10}$ alkylaryl, and —$C_{0-10}$ alkylheterocyclyl.

In one embodiment of the invention, the aryl moiety in $R^1$, is selected from phenyl, naphthyl, phenyl, tetrahydro-naphthyl, indanyl, 2,3-dihydro-1H-indenyl, or biphenyl.

In a subset of this embodiment, the aryl moiety in $R^1$, is selected from phenyl, biphenyl and -2,3-dihydroindenyl.

The heterocyclyl moiety in $R^1$, includes, but is not limited to, the following: azabenzimidazolyl, benzoimidazolyl, benzofuryl, benzofurazanyl, benzopyrazolyl, benzotriazolyl, benzothiophenyl, benzothiazolyl, benzothienyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazolinyl, isoxazolinyl, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzyl, tetrahydrofuryl, tetrahydrothienyl, tetrahydroquinolinyl, 2,3-dihydrobenzofinyl, 2,3-dihydrobenzo-1,4-dioxinyl, imidazo(2,1-b)(1,3) thiazole, pyrimidinylphenyl, pyridinylphenyl, and benzo-1, 3-dioxolyl.

The heterocyclyl moiety in $R^1$, includes, but is not limited to, the following: azabenzimidazolyl, benzoimidazolyl, benzofuranyl, benzopyrazolyl, benzotriazolyl, benzothiophenyl, benzothiazolyl, benzothienyl, benzoxazolyl, carbazolyl, carbolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazolinyl, isoxazolinyl, oxetanyl, pyranyl, pyrazinyl, pyrazolyl, pyridazinyl, pyridazinyl, pyridinyl, pyrimidyl, pyrrolyl, quinazolinyl, quinolyl, tetrahydropyranyl, tetrazolyl, thiadiazolyl, thiazolyl, thienyl, triazolyl, azetidinyl, piperazinyl, piperidinyl, pyrrolidinyl, morpholinyl, thiomorpholinyl, dihydrobenzoimidazolyl, methylenedioxybenzyl, tetrahydrofuranyl, tetrahydrothienyl, tetrahydroquinolinyl, pyrimidinylphenyl, pyridinylphenyl.

In another embodiment, the heterocyclyl moiety in $R^1$ is selected from: pyridinyl, phenyl, thiazolyl, oxadiazolyl, benzothiazolyl, oxazolyl, benzothienyl, pyrazolyl, pyrazinyl, and pyridinyl.

In one embodiment of the present invention, $R^1$ is selected from $—C_{0-10}$ alkylaryl, and $—C_{0-10}$ alkylheterocyclyl.

In one embodiment of the invention, $R^8$ is selected from hydrogen, and $C_{1-6}$ alkyl, optionally substituted with a hydroxy, $—SH$, $—NH_2$ or $—CO_2H$.

In a variant of this embodiment, $R^8$ is hydrogen.

In an embodiment of the present invention, $R^2$ and $R^3$ are each independently selected from hydrogen, and $—C_{1-10}$ alkyl, wherein $C_{1-10}$ alkyl is unsubstituted or substituted with one or more fluorine atoms, and phenyl is unsubstituted or substituted with or more substituents selected from fluoro, chloro, hydroxyl, $C_{1-10}$ alkyl, and $—OC_{1-10}$ alkyl.

In a subset of this embodiment, $R^2$ and $R^3$ are each hydrogen.

In one embodiment, $R^4$, $R^5$, $R^6$, and $R^7$ are independently selected from hydrogen, $—C_1-C_{10}$ alkyl, $(C_{0-10}$ alkyl)aryl, $(C_{0-10}$ alkyl)heterocyclyl, wherein said alkyl, aryl, and heterocyclyl are optionally substituted by one or more substituents $R^9$.

In a subset of the above-mentioned embodiment, $R^4$, $R^5$, $R^6$, and $R^7$ are each hydrogen.

In one embodiment of the invention, X is O, Y is $—CR^4R^5$ and W is $—CR^6R^7$.

In another embodiment, Y is O, X is $—CR^4R^5$ and Z is $—CR^6R^7$.

In yet another embodiment of the invention, W is O, X is $—CR^4R^5$ and X is $—CR^6R^7$.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The Wild "oxo" means "=O". The term "carbonyl" means "C=O."

Structural representations of compounds having substituents terminating with a methyl group may display the terminal methyl group either using the characters "$CH_3$", e.g. "$—CH_3$" or using a straight line representing the presence of the methyl group, e.g., "—" i.e.,

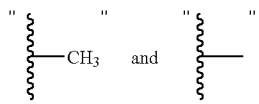

have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

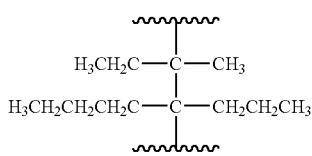

Optical Isomers—Diastereomers—Geometric Isomers—Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts and solvates thereof. Unless specifically mentioned otherwise, reference to one isomer applies to any of the possible isomers. Whenever the isomeric composition is unspecified, all possible isomers are included. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl $—CH_2C(O)—$ groups (keto forms) may undergo tautomerism to form hydroxyl $—CH=C(OH)—$ groups (enol forms). Both keto and enol forms, individually as well as mixtures thereof, are included within the scope of the present invention.

Salts

Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydro-scopicity and solubility. As will be The term "pharmaceutically acceptable salts" refers to salts prepared from pharmaceutically acceptable non-toxic bases or acids. When the compound of the present invention is acidic, its corresponding salt can be conveniently prepared from inorganic bases or organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from organic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylamino-ethanol, ethanolamine, ethylenediamine, N-ethylmorpholine, N-ethylpiperidine, glucamine, glucosamine, histidine, hydrabamine, isopropylamine, dicyclohexylamine, lysine, methyl-glucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from inorganic or organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methane-sulfonic, mucic, nitric, pamoic, pantothenic, phosphoric, succinic, sulfuric, tartaric, p-toluene-sulfonic acid and the like. Preferred are citric, hydrobromic, hydrochloric, maleic, phosphoric, sulfuric, and tartaric acids.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrate includes, but is not limited to, hemi-, mono-, sesqui-, di- and trihydrates.

Prodrugs

The present invention includes within its scope the use of prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound which may not be a compound of formula I, but which converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

Utilities

Compounds of the present invention are inhibitors of hypoxia-inducible factor (HIF) prolyl hydroxylases, and as such are useful in the treatment and prevention of diseases and conditions in which HIF modulation is desirable, such as anemia and ischemia. Compounds of the invention can be used in a selective and controlled manner to induce hypoxia-inducible factor stabilization and to rapidly and reversibly stimulate erythropoietin production and secretion. Accordingly, another aspect of the present invention provides a method of treating or preventing a disease or condition in a mammal, the treatment or prevention of which is effected or facilitated by HIP prolyl hydroxylase inhibition, which comprises administering an amount of a compound of Formula I that is effective for inhibiting HIF prolyl hydroxylase. This aspect of the present invention further includes the use of a compound of Formula I in the manufacture of a medicament for the treatment or prevention of a disease or condition modulated by HIF prolyl hydroxylase.

In one embodiment is a method of enhancing endogenous production of erythropoietin in a mammal which comprises administering to said mammal an amount of a compound of Formula I that is effective for enhancing endogenous production of erythropoietin.

Another embodiment is a method of treating anemia in a mammal which comprises administering to said mammal a therapeutically effective amount of a compound of Formula I. "Anemia" includes, but is not limited to, chronic kidney disease anemia, chemotherapy-induced anemia (e.g., anemia resulting from antiviral drug regimens for infectious diseases, such as HIV and hepatitis C virus), anemia of chronic disease, anemia associated with cancer conditions, anemia resulting from radiation treatment for cancer, anemias of chronic immune disorders such as rheumatoid arthritis, inflammatory bowel disease, and lupus, and anemias due to menstruation or of senescence or in other individuals with iron processing deficiencies such as those who are iron-replete but unable to utilize iron properly.

Another embodiment is a method of treating ischemic diseases in a mammal, which comprises administering to said mammal a therapeutically effective amount of a compound of Formula I.

Combination Therapy

Compounds of Formula I may be used in combination with other drugs that are used in the treatment/prevention/suppression or amelioration of the diseases or conditions for which compounds of Formula 1 are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrastemal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., anemia.

Pharmaceutical Composition

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or a pharmaceutically acceptable salt or solvate thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences,* A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5milliliters contain 100 milligrams of finely divided active ingredient, 100 milligrams of sodium carboxymethyl cellulose, 5milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other active ingredients known to be useful for improving the level of erythropoietin in a patient. Abbreviations Used in the Description of the Preparation of the Compounds of the Present Invention:

AcOH Acetic acid
Aq Aqueous
Brine Saturated aqueous sodium chloride solution
$CDCl_3$ Deuterated Chloroform
$CH_2Cl_2$ Dichloromethane
$CH_3CN$ Acetonitrile
$CO_2Me$ carbomethoxy
DMF N,N-Dimethylformamide
Dppf 1,1"-bis(diphenylphosphino)ferrocene
DBU 1,8-diazabicyclo[5.4.0]undec-7-ene
DIEA N,N-diisopropylethylamine
DMAP 4-N,N-dimethylaminopyridine
DMF N,N-dimethylformamide
DMSO Dimethyl sulfoxide
EtOAc Ethyl acetate
EtOH Ethanol
$Et_2O$ or ether Diethyl ether
G grams
h or hr hour
HCl Hydrochloric acid
HPLC High-performance liquid chromatography
IPA 2-propanol
i-PrOH Isopropyl alcohol
$KHSO_4$ Potassium Sulfate
Mg milligrams
mL milliliters
Mmol millimole
MeCN Acetonitrile
MeOH Methanol
Min minutes
ms or MS Mass pectrum
$Na_2SO_4$ Sodium sulfate
$R_t$ Retention time
t or r Room temperature
TFA Trifluoroacetic acid
THF tetrahydrofuran
μL microliters
Synthesis The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents which are allowed under the definitions of Formula I defined previously.

Intermediates useful for the preparation of the compounds in the present invention are known in the art or may be prepared using chemical methodologies known to those skilled in the art. Examples of reported intermediates include methyl 2-oxotetrahydrofuran-3-carboxylate (IIa), (reported in Rao et. al. *Synth. Commun.* 1989, 19, 1389-93), 4-oxotetrahydrofuran-3-carboxylate (IIb) (reported by Dowd, et. al. *Tetrahedron*, 1991, 47, 4847-4860); and methyl 3-oxotetrahydrofuran-2-carboxylate (IIc) (reported in Rapoport, et. al. *J. Org. Chem.* 1985, 50, 5223-5230).

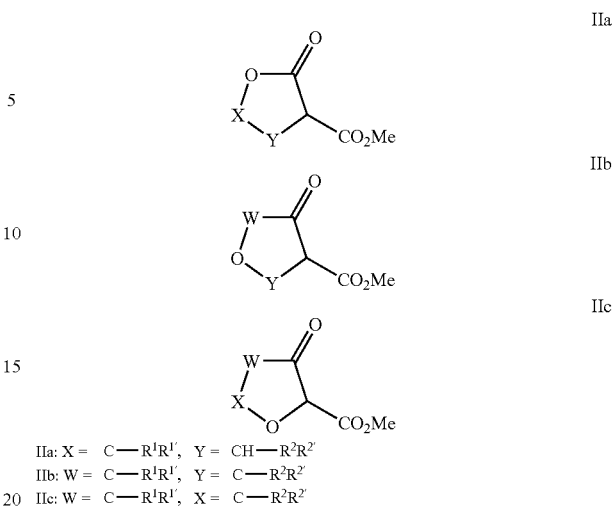

IIa: X = C—R$^1$R$^{1'}$, Y = CH—R$^2$R$^{2'}$
IIb: W = C—R$^1$R$^{1'}$, Y = C—R$^2$R$^{2'}$
IIc: W = C—R$^1$R$^{1'}$, X = C—R$^2$R$^{2'}$

Additionally, patent applications in which the synthesis and use of these types of intermediates (or related analogs thereof) are described have been published (EP 0503844, EP 0505058, US 2005/0256153, US 2006/0079547, US 2006/0234998, US 2007/012335, WO 1994/029295, WO 2005/123744, WO 2007/097929 WO 2007/103905, WO 2007/0213335 and WO 2007/115315). Compounds in the present invention can be conveniently synthesized by those skilled in the art using chemistry detailed in the following schemes.

Scheme 1 outlines the synthesis of tetrahydrofuropyridinecarboxylic acid ester intermediates of type V. The synthesis of the tetrahydrofuropyridine-carboxylic acid esters intermediates can start with the aforementioned keto esters IIa-c, prepared using methods described in the references above. Condensation with substituted amines in the presence of an acid catalyst (e.g. acetic acid) in an appropriate solvent affords the enamines III. The amine moiety in compounds III can be acylated with ethyl malonyl chloride at or below room temperature in the presence of an amine base (e.g. pyridine, triethylamine, N,N-diisopropylethyl-amine) to form the β-carboethoxy amides IV. When treated with a suitable base (e.g. sodium ethoxide, sodium hydride, postassium tert-butoxide) in an appropriate solvent (e.g. ethanol, 1,2-dimethoxyethane, tetrahydrofuran) at either ambient or elevated temperatures, the β-carboethoxy amides IV cyclize to form the desired tetrahydrofuropyridinecarboxylic acid ester intermediates V.

Scheme 1

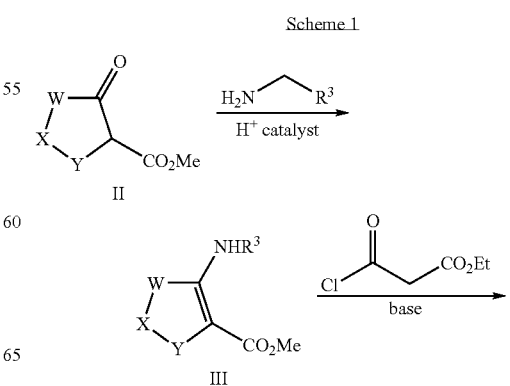

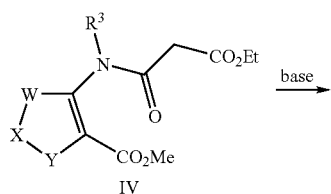

IV

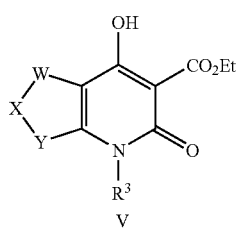

V

W = O and X = C—R¹R¹', Y = C—R²R²'
or
X = O and W = C—R¹R¹', Y = C—R²R²'
or
Y = O and W = C—R¹R¹', X = C—R²R²'

In Scheme 2, the appropriately functionalized tetrahydrofuropyridine carboxylic acid ester V and an α- or β-amino acid ester VI can be coupled in a suitable solvent, (e.g. toluene, xylenes, N,N-dimethylfomamide, ethanol, 1,2-dimethoxyethane) to afford N-acyl α- or β-amino acid esters of type VII. This transformation requires heat, which can be supplied either thermally or through the agency of a microwave. Cleavage of the ester in compounds of type VII affords the desired tetrahydrofuropyridone carboxylic acid I. Conditions for the cleavage of the ester moiety are dependent on the identity of that moiety; general conditions to enact this transformation for different $R^6$ can be found in Greene and Wuts, Eds. *Protective Groups in Organic Synthesis*, $3^{rd}$ Edition, Wiley-Interscience, 1999).

Scheme 2

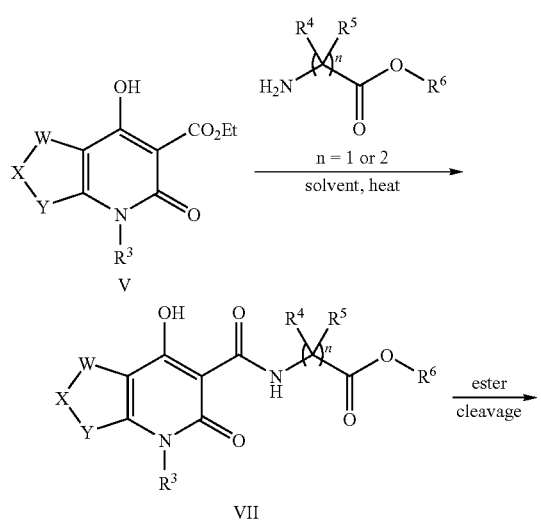

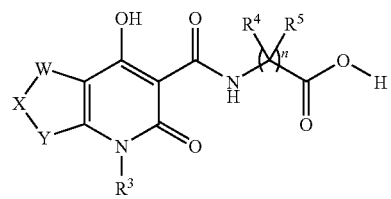

I

W = O and X = C—R¹R¹', Y = C—R²R²'
or
X = O and W = C—R¹R¹', Y = C—R²R²'
or
Y = O and W = C—R¹R¹', X = C—R²R²'

As shown in Scheme 3, N-acyl amino esters of type VII can be further manipulated if the aryl or heterocyclyl substituent in $R_3$ contains a halogen atom. Thus, metal catalyzed cross coupling reactions such as Suzuki, Stile, Negishi, Kumada can be performed with organometallic reagents such as, but not limited to boronic acids, organotin, organozincate, and organomagnesium reagents. General conditions to enact this transformation for different Z and organometallic reagents can be found in Li and Gribble, in *Palladium in Heterocyclic Chemistry*, Tetrahedron Organic Chemisry Series Volume 20, Baldwin and Williams Eds., Pergamon, 2000). The resultant biaryl or heterobiaryl products VIII can be deprotected as described above to afford the desired tetrahydrofuropyridone carboxylic acid I.

Scheme 3

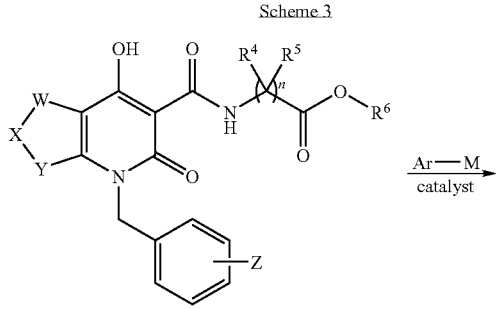

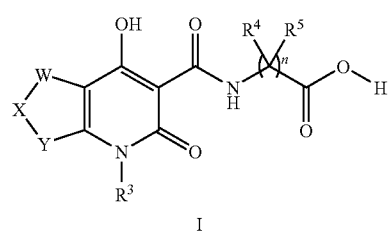

I $W = O$ and $X = C-R^1R^{1'}$, $Y = C-R^2R^{2'}$
or
$X = O$ and $W = C-R^1R^{1'}$, $Y = C-R^2R^{2'}$
or
$Y = O$ and $W = C-R^1R^{1'}$, $X = C-R^2R^{2'}$
$Z$ = halogen; $Z'$ = Aryl, heteroaryl There may be cases where $R^1$-$R^5$ of I contain one or more asymmetric centers. When this occurs, the individual stereoisomers of I can obtained by methods known to those skilled in the art which include (but are not limited to): stereospecific synthesis, resolution of salts of I or any of the intermediates used in its preparation with enantiopure acids or bases, resolution of I or any of the intermediates used in its preparation by HPLC employing enantiopure stationary phases.

GENERAL EXPERIMENTAL COMMENTS

In the following examples, $^1$H-NMR spectra were obtained on a 500 MHz VARIAN Spectrometer in $CDCl_3$ or $CD_3OD$ as indicated and chemical shifts are reported as δ using the solvent peak as reference and coupling constants are reported in hertz (Hz). HPLC/MS data was generated using a MICROMASS ZMD mass spectrometer coupled to an AGILENT 1100 Series HPLC under the following conditions:

Method A:

Waters XTerra, 5µ, 4.6×50 mm column, gradient 10:90-95:5 v/v $CH_3CN$:$H_2O$+0.05% TFA over 3.25 min, then hold at 95:5 v/v $CH_3CN$:$H_2O$+0.05% TFA for 0.35 min; flow rate 2.5 mL/min, diode array detection 200-400 nM.

Method B:

Waters XTerra, 5µ, 4.6×50 mm column, gradient 10:90-95:5 v/v $CH_3CN$:$H_2O$+0.05% TFA over 1.25 min, then hold at 95:5 v/v $CH_3CN$:$H_2O$+0.05% TFA for 0.35 min; flow rate 2.5 mL/min, diode array detection 200-400 nM.

Example 1

N-((4-benzyl-7-hydroxy-3-methyl-5-oxo-4,5-dihydrothieno[3,2-b]pyridin-6-yl)carbonyl)glycine (1-5)

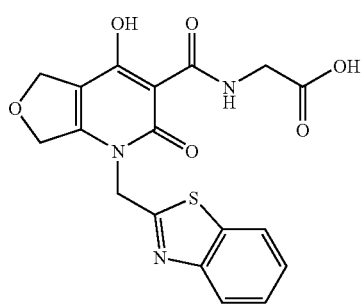

1-5

Step A Methyl 4-[(1,3-benzothiazol-2ylmethyl)amino]-2,5-dihydrofuran-3-carboxylate (1-1)

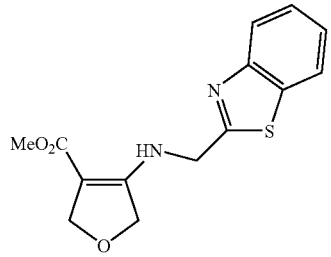

1-1

To a solution of methyl-4-oxo-tetrahydrofuro-3-carboxylate (1.18 g, 8.19 mmol) in ethanol (5mL), 1-(1,3-benzothiazol-2-yl)methanamine hydrochloride (1.73 g, 8.60 mmol), triethylamine (1.20 mL, 8.60 mmol) and acetic acid (47 µL, 0.819 mmol) were added and the reaction mixture was heated to reflux for 6 hr, cooled to ambient temperature and concentrated in vacuo. The resultant residue was partitioned between EtOAc (10 mL) and $H_2O$ (5mL) and the organic layer was washed with $KHSO_4$ (1×5 mL), $NaHCO_3$ (1×5 mL) brine (1×5 mL), dried over $MgSO_4$, filtered and concentrated in vacuo. Purification by flash chromatography 10, 15% EtOAc/hexanes on $SiO_2$ (40 S+ column) afforded 610 mg of an orange foam: $^1$H NMR (500 MHz, $CDCl_3$) δ 3.73 (s, 3 H), 4.67 (d, 2 H, J=6.8 Hz), 4.80 (s, 4 H), 7.40 (t, 1 H, J=7.5 Hz), 7.50 (t, 1 H, J=7.2 Hz), 7.87 (d, 1 H, J=8.0 Hz), 7.99 (d, 1 H, J=8.2 Hz).

Step B Methyl-4-[(1,3-benzothiazol-2-ylmethyl)(3-ethoxy-3-oxopropanoyl)amino]-2,5 dihydrofuran-3-carboxylate (1-2)

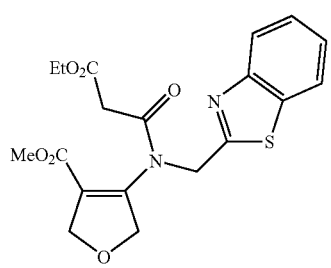

1-2

To an ice-cold solution of the enamine from step A (610 mg, 2.10 mmol) and pyridine (20 µL, 2.53 mmol) in dichloromethane (6 mL), ethyl malonyl chloride (323 µL, 2.53 mmol) was added dropwise. The ice bath was removed and the reaction mixture stirred at ambient temperature. After 1.5 hr, the reaction mixture was diluted with dichloromethane (10 mL) and washed with 5% $KHSO_4$ (3×5 mL), saturated $NaHCO_3$ (1×5 mL) and brine (1×5 mL). The organic layer was dried over $MgSO_4$, filtered and concentrated in vacuo. The residue was purified by flash chromatography (10-30% EtOAc/hexanes) on $SiO_2$ (40S+column) to afford compound 1-2as a colorless oil, 454 mg: $^1$H NMR (500 MHz, $CDCl_3$): δ 1.26 (t, 3H, J=7.1 Hz), 3.54 (s, 2 H), 3.59 (s, 3 H), 4.18 (q, 2 H, J=7.1 Hz), 4.76 (br s, 2 H), 4.89 (t, 2 H, J=5.0 Hz), 5.14 (s, 2 H), 7.40 (t, 2 H, J=7.4 Hz), 7.48 (t, 1 H, J=7.3 Hz), 7.86 (d, 1 H, J=8.2 Hz), 7.97 (d, 1 H, J=8.2 Hz).

Step C Ethyl 1-(1,3-benzothiazol-2-ylmethyl)-4-hydroxy-2-oxo-1,2,5,7-tetrahydrofuro[3,4-b]pyridin-3-carboxylate (1-3)

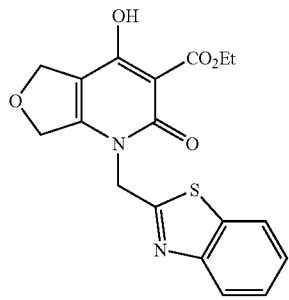

1-3

A solution of the amido ester from step B (450 mg, 1.11 mmol) in 1,2-dimethoxyethane (DME) (4.5 mL), was added 60% sodium hydride (44.5 mg of 1.11 mmol) and the resultant solution was stirred at ambient temperature. After 2 Hr, the reaction mixture was quenched with sat. NaH$_2$PO$_4$ (5mL), diluted with H$_2$O (2mL). The solids were filtered, washed with H$_2$O (2×2 mL) and dried in vacua to furnish 241 mg of compound 1-3 as an off white solid: $^1$H NMR (500 MHz, DMSO-d$_6$): δ 1.23 (t, 3 H, J=7.1 Hz), 4.20 (q, 2 H, J=7.1 Hz), 4.91 (t, 2 H, J=2.8 Hz), 5.08 (t, 2 H, J=2.7 Hz), 5.31 (s, 2 H), 7.43 (t, 1 H, J=7.5 Hz), 7.50 (t, 1 H, J=7.6 Hz), 7.96 (d, 1 H, J=8.0 Hz), 8.06 (d, 1 H, J=8.0 Hz); HPLC/MS: 3.05 min, 373.0 (M+H)$^+$.

Step D tert-Butyl-N-({4-hydroxy-2-oxo-1-[4-(trifluoromethyl)benzyl]-1,2,5,7-tetrahydrofuro[3,4-b]pyridin-3-yl}carbonyl)glycinate (1-4)

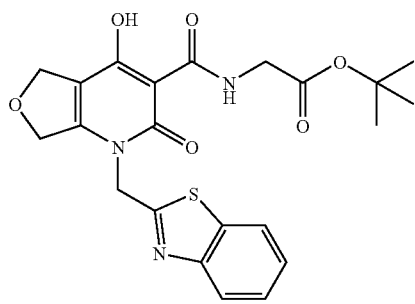

1-4

To a solution of the ester from step C (119 mg, 0.320 mmol) in DME (3 mL), tert-butyl glycine (52 μL, 0.383 mmol) was added and the mixture was heated to 150° C. in the microwave for 20 min. The reaction mixture was cooled to ambient temperature, diluted with EtOAc (10 mL) and the organic layer was washed with KHSO$_4$ (1×5 mL), NaHCO$_3$ (1×5 mL) brine (1×5 mL), dried over MgSO$_4$, filtered and concentrated in vacua. Purification of the residue by flash chromatography 10, 20, 30% acetone/hexanes on SiO$_2$ (25S+column) afforded compound 1-4 as a white solid, 779 mg: $^1$H NMR (500 MHz, DMSO-d$_6$): δ 1.40 (s 9 H), 4.02 (d, 2 H, J=5.7 Hz), 4.99 (t, 2 H, J=3.0 Hz), 5.19 (t, 2 H, J=3.0 Hz), 5.46 (s, 2 H), 7.44 (t, 1 H, J=7.1 Hz), 7.49 (t, 1 H, J=7.1 Hz), 7.97 (d, 1 H, J=8.2 Hz), 8.07 (d, 1 H, J=7.8 Hz); HPLC/MS: 2.15 min; 458.1 (M+H)$^+$.

Step E N-{[1-(1,3-benzothiazol-2-ylmethyl)-4-hydroxy-2-oxo-1,2,5,7-tetrahydrofuro[3,4-b]-pyridin-3-yl]carbonyl}glycine (1-5)

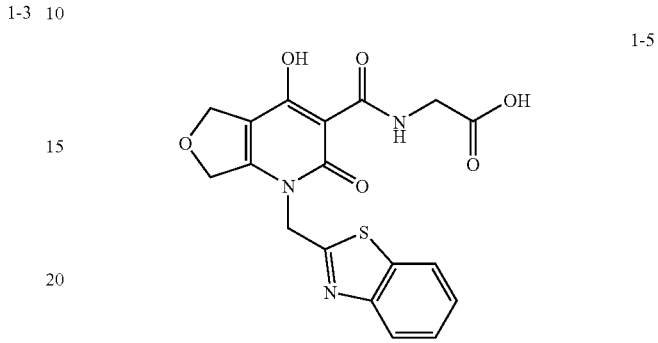

1-5

TFA (0.75 mL) was added to a solution of the tert-butyl ester, 1-4, from step D (79 mg, 0.173 mmol) in dichloromethane (1.5 mL), and the reaction mixture stirred at ambient temperature. After 15 hr, the reaction mixture was concentrated in vacuo and the residue azeotroped with 1,2-dichloroethane (2×2 mL). The resultant solids were diluted with ET$_2$O and filtered. Washed the solids with Et$_2$O (3×5 mL) and air dried to give 64 mg of the title compound, 1-5, as an off-white solid: $^1$H NMR (500 MHz, DMSO-d$_6$): δ 4.06 (d, 2 H, J=5.7 Hz), 4.99 (t, 2 H, J=3.0 Hz), 5.18 (t, 2 H, J=3.0 Hz), 5.46 (s, 2 H), 7.44 (t, 1 H, J=7.1 Hz), 7.49 (t, 1 H, J=7.1 Hz), 7.97 (d, 1 H, J=8.0 Hz), 8.07 (d, 1 H, J=7.7 Hz);10.14 (t, 1 H, J=5.5 Hz), 12.95 (br s, 1H); HPLC/MS; 1.63 min; 402.1 (M+H)$^+$.

Example 2

N-({4-hydroxy-2-oxo-4-[4-(trifluoromethyl)benzyl]-1,2,5,7-tetrahydrofuro[3,4-b]pyridin-3-yl}carbonyl)glycine (2-1)

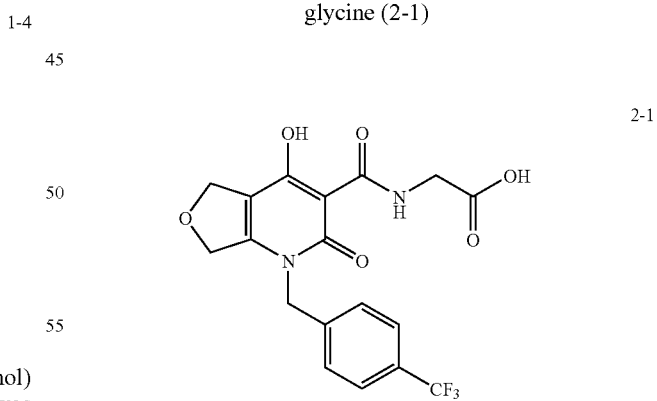

2-1

The title compound, 2-1, was prepared in a manner analogous to that described for EXAMPLE 1, substituting for 4-trifluoromethylbenzylamine for 1-(1,3-benzothiazol-2-yl) methanamine in step A. $^1$H NMR (500 MHz, DMSO-d$_6$): δ 4.05 (d, 2 H, J=5.5 Hz), 4.96 (t, 2 H, J=2.8 Hz), 5.01 (t, 2 H, 2.8 Hz), 5.14 (s, 2 H), 7.43 (d, 2 H, J=8.0 Hz), 7.70 (d, 2 H, J=8.3 Hz), 10.2 (t, 1 H J=5.5 Hz), 12.80 (br s, 1 H); HPLC/MS; 1.33 min; 413.2 (M+H)$^+$.

Examples 3-27

The following compounds were prepared by using procedures analogous to those described for EXAMPLE 1, substituting an appropriate keto ester and substituted amine for methyl-4-oxo-tetrahydrofuro-3-carboxylate and 1-(1,3-benzothiazol-2-yl)methanamine hydrochloride respectively, as outlined in Step A.

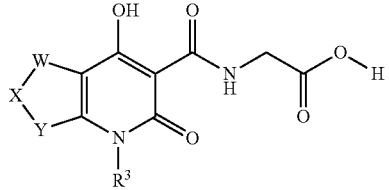

| EXAMPLE | W | X | Y | R3 | HPLC A/B (min) | MS m/z (M + H) |
|---|---|---|---|---|---|---|
| 3 | CH$_2$ | O | CH$_2$ | 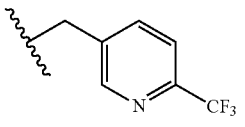 [SMILES: *Cc1ccc(C(F)(F)F)nc1] | 1.07 A | 414.2 |

N-[(4-hydroxy-2-oxo-1-{[6-(trifluoromethyl)pyridine-3-yl]methyl}-1,2,5,7-tetrahydrofuro[3,4-b]pyridin-3-yl)carbonyl]glycine
$^1$H NMR (500 MHz, DMSO-d$_6$): δ 4.04 (d, 2 H, J = 5.5 Hz), 4.96 (t, 2 H, J = 2.8 Hz), 5.09 (s, 2 H), 5.15 (t, 2 H, J = 2.8 Hz), 7.85 (d, 2 H, J = 8.0 Hz), 7.90 (d, 2 H, J = 8.2 Hz), 8.72 (s, 1 H), 10.14 (t, 1 H, J = 5.5 Hz), 12.87 (s, 1 H).

| | | | | | | |
|---|---|---|---|---|---|---|
| 4 | CH$_2$ | O | CH$_2$ | 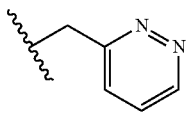 [SMILES: *Cc1cccnn1] | 0.81 A | 347.2 |

N-{[4-hydroxy-2-oxo-1-(pyridazin-3-ylmethyl)-1,2,5,7-tetrahydrofuro[3,4-b]pyridin-3-yl]carbonyl}glycine
$^1$H NMR (500 MHz, DMSO-d$_6$): δ 4.02 (d, 2 H, J = 5.5 Hz), 5.00 (t, 2 H, J = 2.8 Hz), 5.13 (t, 2 H, J = 2.8 Hz), 5.26 (s, 2 H), 7.69 (d, 2 H, J = 8.5 Hz), 7.90 (d, 2 H, J = 8.5 Hz), 9.15 (d, 1 H, J = 6.4 Hz), 10.12 (t, 1 H, J = 5.5 Hz), 12.81 (s, 1 H).

| | | | | | | |
|---|---|---|---|---|---|---|
| 5 | CH$_2$ | O | CH$_2$ | 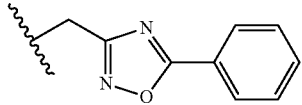 [SMILES: *Cc1noc(-c2ccccc2)n1] | 1.10 A | 314.1 |

N-({4-hydroxy-2-oxo-1-[(5-phenyl-1,2,4-oxadiazol-3-yl)methyl]-1,2,5,7-tetrahydrofuro[3,4-b]pyridin-3-yl}carbonyl)glycine
$^1$H NMR (500 MHz, DMSO-d$_6$): δ 4.05 (d, 2 H, J = 5.1 Hz), 5.00 (t, 2 H, J = 2.8 Hz), 5.19 (t, 2 H, J = 2.8 Hz), 5.27 (s, 2 H), 7.62 (t, 2 H, J = 7.7 Hz), 7.70 (t, 1 H, J = 7.7 Hz), 8.06 (d, 2 H, J = 8.7 Hz), 10.12 (t, 1 H, J = 5.5 Hz), 12.85 (s, 1 H).

| | | | | | | |
|---|---|---|---|---|---|---|
| 6 | CH$_2$ | O | CH$_2$ | 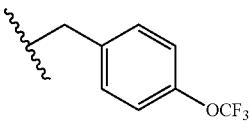 [SMILES: *Cc1ccc(OC(F)(F)F)cc1] | 1.14 A | 429.0 |

N-({4-hydroxy-2-oxo-1-[4-(trifluoromethoxy)benzyl]-1,2,5,7-tetrahydrofuro[3,4-b]pyridin-3-yl}carbonyl)glycine
$^1$H NMR (500 MHz, DMSO-d$_6$): δ 4.06 (d, 2 H, J = 5.5 Hz), 4.95 (t, 2 H, J = 2.7 Hz), 5.02 (t, 2 H, J = 3.0 Hz), 5.08 (s, 2 H), 7.35 (q, 4 H, J = 8.7 Hz), 10.24 (t, 1 H, J = 5.5 Hz), 12.84 (s, 1 H).

| | | | | | | |
|---|---|---|---|---|---|---|
| 7 | CH$_2$ | O | CH$_2$ | 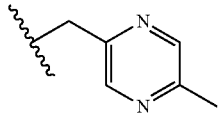 [SMILES: *Cc1cnc(C)cn1] | 0.97 A | 361.1 |

N-({4-hydroxy-1-[(5-methylpyrazin-2-yl)methyl]-2-oxo-1,2,5,7-tetrahydrofuro[3,4-b]pyridin-3-yl}carbonyl)glycine
$^1$H NMR (500 MHz, DMSO-d$_6$): δ 2.45 (s, 3H), 4.01 (d, 2 H, J = 5.5 Hz), 4.99 (t, 2 H, J = 2.7 Hz), 5.10 (s, 2 H), 5.14 (t, 2 H, J = 3.0 Hz), 8.44 (s, 1 H), 8.61 (s, 1 H), 10.15 (t, 1 H, J = 5.5 Hz), 12.82 (s, 1 H).

-continued

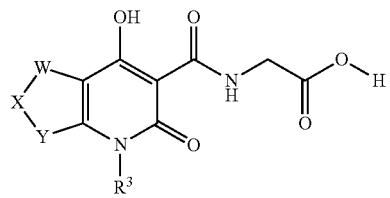

| EXAMPLE | W | X | Y | R₃ | HPLC A/B (min) | MS m/z (M + H) |
|---|---|---|---|---|---|---|
| 8 | CH₂ | O | CH₂ | 4-isopropoxybenzyl | 1.14 A | 403.1 |

N-{[4-hydroxy-1-(4-isopropoxybenzyl)-2-oxo-1,2,5,7-tetrahydrofuro[3,4-b]pyridin-3-yl]carbonyl}glycine
$^1$H NMR (500 MHz, DMSO-d$_6$): δ 1.22 d, 6 H, J = 6.0 Hz 4.07 (d, 2 H, J = 5.5 Hz), 4.56 (septet, 1 H, J = 6.0 Hz), 4.92 (t, 2 H, J = 2.7 Hz), 4.98 (s, 2 H), 5.01 (t, 2 H, J = 2.9 Hz), 6.86 (d, 2 H, J = 7.8 Hz), 7.16 (d, 2 H, J = 7.8 Hz), 10.31 (t, 1 H, J = 5.5 Hz), 12.84 (s, 1H).

| 9 | CH₂ | O | CH₂ | (6-chloropyridin-3-yl)methyl | 2.48 B | 380.1 |

N-({1-[(6-chloropyridin-3-yl)methyl]-4-hydroxy-2-oxo-1,2,5,7-tetrahydrofuro[3,4-b]pyridin-3-yl}carbonyl)glycine
$^1$H NMR (500 MHz, DMSO-d$_6$): δ 4.05 (d, 2 H, J = 5.5 Hz), 4.95 (t, 2 H, J = 2.7 Hz), 5.04 (s, 2 H), 5.08 (t, 2 H, J = 2.8 Hz), 7.47 (d, 1 H, J = 8.3 Hz), 7.73 (dd, 1 H, J = 2.5, 8.3 Hz), 8.38 (d, 1 H, J = 2.3 Hz), 10.17 (t, 1 H, J = 5.5 Hz), 12.81 (s, 1 H).

| 10 | CH₂ | O | CH₂ | 4-bromobenzyl | 1.13 A | 424.0 |

N-{[1-(4-bromobenzyl)-4-hydroxy-2-oxo-1,2,5,7-tetrahydrofuro[3,4-b]pyridin-3-yl]carbonyl}glycine
$^1$H NMR (500 MHz, DMSO-d$_6$): δ 4.06 (d, 2 H, J = 5.5 Hz), 4.94 (m, 2 H), 5.00 (m, 2 H), 5.03 (m, 2 H), 7.20 (d, 2 H, J = 8.5 Hz), 7.54 (d, 2 H, J = 8.5 Hz), 10.25 (t, 1 H, J = 5.5 Hz), 12.85 (s, 1 H).

| 11 | CH₂ | O | CH₂ | 2,3-dihydro-1H-inden-2-ylmethyl | 1.15 A | 385.1 |

N-{[1-(2,3-dihydro-1H-inden-2-ylmethyl)-4-hydroxy-2-oxo-1,2,5,7-tetrahydrofuro[3,4-b]pyridin-3-yl]carbonyl}glycine
$^1$H NMR (500 MHz, DMSO-d$_6$): δ 2.63-2.68 (m, 2 H), 2.87-2.93 (m, 3 H), 3.85 (d, 2 H, J = 6.2 Hz), 4.06 (d, 2 H, J = 5.7 Hz), 4.95 (t, 2 H, J = 2.7 Hz), 5.04 (t, 2 H, J = 2.8 Hz), 7.10-7.13 (m, 2 H), 7.20 (d, 2 H, J = 8.3 Hz), 10.34 (t, 1 H, J = 5.5 Hz), 12.86 (s, 1 H).

| 12 | CH₂ | O | CH₂ | (5-chloropyrazin-2-yl)methyl | 2.57 B | 381.1 |

N-({1-[(5-chloropyrazin-2-yl)methyl]-4-hydroxy-2-oxo-1,2,5,7-tetrahydrofuro[3,4-b]pyridin-3-yl}carbonyl)glycine
$^1$H NMR (500 MHz, DMSO-d$_6$): δ 4.01 (d, 2 H, J = 5.8 Hz), 4.99 (t, 2 H, J = 2.8 Hz), 5.12 (t, 2 H, J = 2.9 Hz), 5.16 (s, 2 H), 8.64 (d, 1 H, J = 1.2 Hz), 8.72 (d, 1 H, J = 1.1 Hz), 10.08 (t, 1 H, J = 5.7 Hz), 12.82 (s, 1 H).

-continued

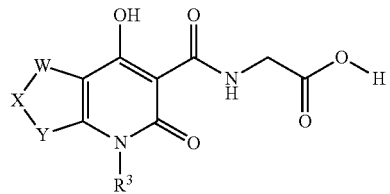

| EX-AMPLE | W | X | Y | R₃ | HPLC A/B (min) | MS m/z (M + H) |
|---|---|---|---|---|---|---|
| 13 | CHCH₃ | O | CH₂ | 4-(trifluoromethyl)benzyl | 3.25 B | 427.2 |

N-({4-hydroxy-5-methyl-2-oxo-1-[4-(trifluoromethyl)benzyl]-1,2,5,7-tetrahydrofuro[3,4-b]pyridin-3-yl}carbonyl)glycine
$^1$H NMR (500 MHz, DMSO-d$_6$): δ 1.41, (d, 3 H, J = 6.2 Hz), 4.04 (d, 2 H, J = 5.7 Hz), 4.90 (dd, 1 H, J = 2.0, 14.7 Hz), 5.04-5.30 (m, 4 H), 7.43 (d, 2 H, J = 8.2 Hz), 7.70 (d, 2 H, J = 8.2 Hz), 10.20 (t, 1 H, J = 5.3 Hz), 12.85 (s, 1 H).

| 14 | CHCH₃ | O | CH₂ | [6-(trifluoromethyl)pyridin-3-yl]methyl | 2.90 B | 428.2 |

N-[(4-hydroxy-5-methyl-2-oxo-1-{[6-(trifluoromethyl)pyridine-3-yl]methyl}-1,2,5,7-tetrahydrofuro[3,4-b]pyridin-3-yl)carbonyl]glycine
$^1$H NMR (500 MHz, DMSO-d$_6$): δ 1.42, (d, 3 H, J = 6.2 Hz), 4.04 (d, 2 H, J = 5.5 Hz), 5.00 (dd, 1 H, J = 2.1, 14.9 Hz), 5.01-5.30 (m, 4 H), 7.85 (d, 1 H, J = 8.3 Hz), 7.90 (d, 1 H, J = 8.5 Hz), 8.72, (s, 1 H), 10.20 (t, 1 H, J = 5.3 Hz), 12.80 (s, 1 H).

| 15 | CH₂ | O | CH₂ | 4-bromo-2-fluorobenzyl | 1.15 A | 442.0 |

N-{[1-(4-bromo-2-fluorobenzyl)-4-hydroxy-2-oxo-1,2,5,7-tetrahydrofuro[3,4-b]pyridin-3-yl]carbonyl}glycine
$^1$H NMR (500 MHz, DMSO-d$_6$): δ 4.03 (d, 2 H, J = 5.7 Hz), 4.96 (t, 2 H, J = 2.8 Hz), 5.01 (s, 2 H), 5.04 (t, 2 H, J = 2.8 Hz), 7.09 (t, 1 H, J = 8.2 Hz), 7.37 (dd, 1 H, J = 1.8, 8.4 Hz), 7.57 (dd, 1 H, J = 1.7, 9.9 Hz), 10.13 (t, 1 H, J = 5.5 Hz), 12.84 (s, 1 H).

| 16 | CH₂ | O | CH₂ | 2-chlorobenzyl | 1.12 A | 379.1 |

N-{[1-(3-chlorobenzyl)-4-hydroxy-2-oxo-1,2,5,7-tetrahydrofuro[3,4-b]pyridin-3-yl]carbonyl}glycine
$^1$H NMR (500 MHz, DMSO-d$_6$): δ 4.03 (d, 2 H, J = 5.7 Hz), 4.97-4.99 (m, 4 H), 5.10 (s, 2 H), 6.88 (d, 1 H, J = 8.4 Hz), 7.27-7.33 (m, 2 H), 7.49-7.51 (m, 1 H), 10.16 (t, 1 H, J = 5.5 Hz), 12.85 (s, 1 H).

| 17 | CH₂ | O | CH₂ | 4-(difluoromethoxy)benzyl | 1.12 A | 411.1 |

N-{[1-(4-difluoromethoxybenzyl)-4-hydroxy-2-oxo-1,2,5,7-tetrahydrofuro[3,4-b]pyridin-3-yl]carbonyl}glycine
$^1$H NMR (500 MHz, DMSO-d$_6$): δ 4.05 (d, 2 H, J = 5.5 Hz), 4.94, (s, 2 H), 5.00-5.04 (m, 2 H), 7.13 (d, 2 H, J = 8.4 Hz), 7.30 (d, 2 H, J = 8.5 Hz), 10.26 (t, 1 H, J = 5.5 Hz), 12.86 (s, 1 H).

-continued

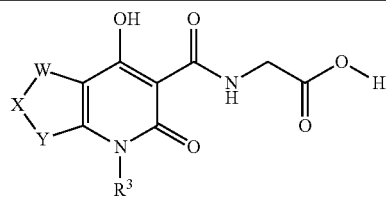

| EX-AMPLE | W | X | Y | R₃ | HPLC A/B (min) | MS m/z (M + H) |
|---|---|---|---|---|---|---|
| 18 | CH₂ | O | CH₂ | 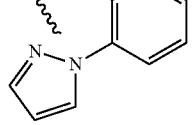 | 1.12 A | 411.1 |

N-({4-hydroxy-2-oxo-1-[3-(1H-pyrazole-1-yl)benzyl]-1,2,5,7-tetrahydrofuro[3,4-b]pyridin-3-yl}carbonyl)glycine
$^1$H NMR (500 MHz, DMSO-d$_6$): δ 4.02 (d, 2 H, J = 5.5 Hz), 4.84 (t, 2 H, J = 2.8 Hz), 4.95 (t, 2 H, J = 2.6 Hz), 5.00 (s, 2 H), 6.56 (d, 1 H, J = 2.3 Hz), 7.00 (d, 1 H, J = 7.6 Hz), 7.37-7.46 (m, 3 H), 7.79 (s, 1 H), 8.20 (d, 1 H, J = 2.3 Hz), 10.15 (t, 1 H, J = 5.5 Hz), 12.81 (s, 1 H).

| 19 | CH₂ | O | CH₂ | 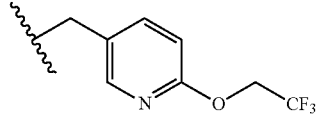 [SMILES: *Cc1ccc(OCC(F)(F)F)nc1] | 1.32 A | 444.1 |

N-[(4-hydroxy-2-oxo-1-{[6-(2,2,2-trifluoroethoxy)pyridin-3-yl]methyl}-1,2,5,7-tetrahydrofuro[3,4-b]pyridin-3-yl)carbonyl]glycine
$^1$H NMR (500 MHz, DMSO-d$_6$): δ 4.06 (d, 2 H, J = 5.7 Hz), 4.94-5.00 (m, 4 H), 5.10 (t, 2 H, J = 3.0 Hz), 6.96 (d, 1 H, J = 8.6 Hz), 7.73 (dd, 2 H, J = 2.4, 8.6 Hz), 8.18 (d, 1 H, J = 2.3 Hz), 10.26 (t, 1 H, J = 5.5 Hz), 12.80 (s, 1 H).

| 20 | CH₂ | O | CH₂ | 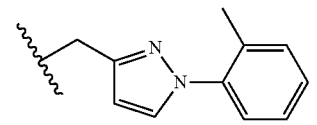 [SMILES: *Cc1ccn(-c2ccccc2C)n1] | 1.10 A | 425.2 |

N-[(4-hydroxy-1-{[1-(2-methylphenyl)-1-H-pyrazol-3-yl]methyl}-2-oxo-1,2,5,7-tetrahydrofuro[3,4-b]pyridin-3-yl)carbonyl]glycine
$^1$H NMR (500 MHz, DMSO-d$_6$): δ 2.18 (s, 3 H), 4.06 (d, 2 H, J = 5.7 Hz), 4.93 (s, 4 H), 5.19 (s, 2 H), 7.28-7.37 (m, 4 H), 7.72 (s, 1 H), 8.08 (s, 1 H), 10.33 (t, 1 H, J = 5.5 Hz), 12.85 (s, 1 H).

| 21 | CH₂ | O | CH₂ | 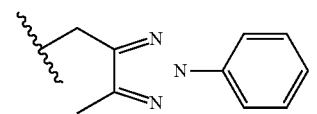 | 1.16 A | 425.2 |

N-({4-hydroxy-1-[(5-methyl-2-phenyl-2H-1,2,3-triazol-4-yl)methyl]-2-oxo-1,2,5,7-tetrahydrofuro[3,4-b]pyridin-3-yl}carbonyl)glycine
$^1$H NMR (500 MHz, DMSO-d$_6$): δ 2.41 (s, 3 H), 4.05 (d, 2 H, J = 5.7 Hz), 4.98 (t, 2 H, J = 2.7 Hz), 5.13 (s, 2 H), 5.29 (t, 2 H, J = 2.8 Hz), 7.34-7.38 (m, 1 H), 7.51 (t, 2 H, J = 8.5 Hz) 7.88 (d, 2 H, J = 2.8 Hz), 10.18 (t, 1 H, J = 5.5 Hz), 12.82 (s, 1 H).

| 22 | CH₂ | O | CH₂ | 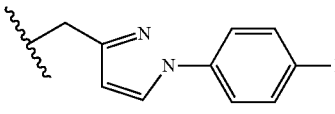 | 1.12 A | 429.1 |

N-[(1-{[1-(4-fluorophenyl)-1H-pyrazol-3-yl]methyl-4-hydroxy-2-oxo-1,2,5,7-tetrahydrofuro[3,4-b]pyridin-3-yl)carbonyl]glycine
$^1$H NMR (500 MHz, DMSO-d$_6$): δ 4.06 (d, 2 H, J = 5.5 Hz), 4.90 (s, 2 H), 4.94 (t, 2 H, J = 2.8 Hz), 5.22 (t, 2 H, J = 2.8 Hz), 7.32 (d, 2 H, J = 8.8 Hz), 7.75 (s, 1 H), 7.79-7.84 (m, 2 H), 8.47 (s, 1 H), 10.31 (t, 1 H, J = 5.6 Hz), 12.85 (s, 1 H).

-continued

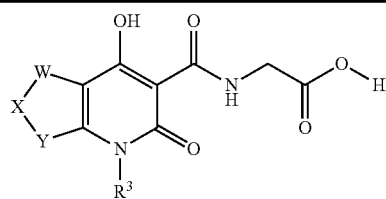

| EX-AMPLE | W | X | Y | R₃ | HPLC A/B (min) | MS m/z (M + H) |
|---|---|---|---|---|---|---|
| 23 | CH₂ | O | CH₂ | 4-(1,3-thiazol-2-yl)benzyl | 1.11 A | 428.1 |

N-({4-hydroxy-2-oxo-1-[4-(1,3-thiazol-2-yl)benzyl]-1,2,5,7-tetrahydrofuro[3,4-b]pyridin-3-yl}carbonyl)glycine
¹H NMR (500 MHz, DMSO-d₆): δ 4.06 (d, 2 H, J = 5.7 Hz), 4.95 (t, 2 H, J = 2.8 Hz), 5.03 (t, 2 H, J = 2.9 Hz), 5.12 (s, 2 H), 7.32 (d, 2 H, J = 7.6 Hz), 7.77 (d, 1 H, J = 3.2 Hz), 7.90-7.94 (m, 2 H), 10.26 (t, 1 H, J = 5.6 Hz), 12.86 (s, 1 H).

| 24 | CH₂ | O | CH₂ | 4-(2,2,2-trifluoroethoxy)benzyl | 1.13 A | 443.1 |

N-({4-hydroxy-2-oxo-1-[4-(2,2,2-trifluoroethoxy)benzyl]-1,2,5,7-tetrahydrofuro[3,4-b]pyridin-3-yl}carbonyl)glycine
¹H NMR (500 MHz, DMSO-d₆): δ 4.06 (d, 2 H, J = 5.7 Hz), 4.72 (q, 2 H, J = 8.9 Hz), 4.93 (t, 2 H, J = 2.7 Hz), 5.00 (s, 4 H), 7.01 (d, 2 H, J = 8.6 Hz), 7.23 (d, 2 H, J = 8.5 Hz), 10.29 (t, 1 H, J = 5.5 Hz), 12.84 (s, 1 H).

| 25 | CH₂ | O | C(CH₃)₂ | 1,3-benzothiazol-2-ylmethyl | 3.00 B | 430.1 |

N-{[(1-(1,3-benzothiazol-2-ylmethyl)-4-hydroxy-7,7-dimethyl-2-oxo-1,2,5,7-tetrahydrofuro[3,4-b]pyridin-3-yl]carbonyl)glycine
¹H NMR (500 MHz, DMSO-d₆): δ 1.53 (s, 6 H), 4.06 (d, 2 H, J = 5.6 Hz), 4.86 (s, 2 H), 5.57 (s, 2 H), 7.42 (t, 1 H, J = 7.1 Hz), 7.48 (t, 1 H, J = 7.3 Hz), 7.95 (d, 1 H, J = 8.0 Hz), 8.07 (d, 1 H, J = 7.8 Hz); 10.8 (t, 1 H, J = 5.6 Hz), 12.80 (br s, 1H).

| 26 | CH₂ | O | CH₂ | [4-(2,4-dichlorophenyl)-1,3-thiazol-2-yl]methyl | 3.57 B | 496.1 |

N-[(1-{[4-(2,4-dichlorophenyl)-1,3-thiazol-2-yl]methyl}-4-hydroxy-2-oxo-1,2,5,7-tetrahydrofuro[3,4-b]pyridin-3-yl)carbonyl]glycine
¹H NMR (500 MHz, DMSO-d₆): δ 4.06 (d, 2 H, J = 5.5 Hz), 4.97 (t, 2 H, J = 2.7 Hz), 5.25 (t, 2 H, J = 2.9 Hz), 5.37 (s, 2 H), 7.53 (dd, 1 H, J = 2.2, 8.4 Hz), 7.72 (d, 1 H, J = 2.0 Hz), 7.82 (d, 1 H, J = 8.4 Hz), 8.11 (s, 1 H), 10.16 (t, 1 H, J = 5.5 Hz), 12.84 (s, 1 H).

| 27 | CH₂ | O | CH₂ | [4-(2-chlorophenyl)-1,3-thiazol-2-yl]methyl | 3.28 B | 462.1 |

N-[(1-{[4-(2-chlorophenyl)-1,3-thiazol-2-yl]methyl}-4-hydroxy-2-oxo-1,2,5,7-tetrahydrofuro[3,4-b]pyridin-3-yl)carbonyl]glycine
¹H NMR (500 MHz, DMSO-d₆): δ 4.06 (d, 2 H, J = 5.4 Hz), 4.97 (t, 2 H, J = 2.7 Hz), 5.26 (t, 2 H, J = 2.8 Hz), 5.37 (s, 2 H), 7.37-7.44 (m, 2 H), 7.55 (dd, 1 H, J = 1.1, 7.8 Hz), 7.79 (dd, 1 H, J = 1.7, 7.8 Hz), 8.06 (s, 1 H), 10.17 (t, 1 H, J = 5.5 Hz), 12.82 (s, 1 H).

Example 28

N-({1-[2'-chlorophenyl-4-yl)methyl]-4-hydroxy-2-oxo-1,2,5,7-tetrahydrofuro[3,4-b]pyridin-3-yl}carbonyl)glycine (28-6)

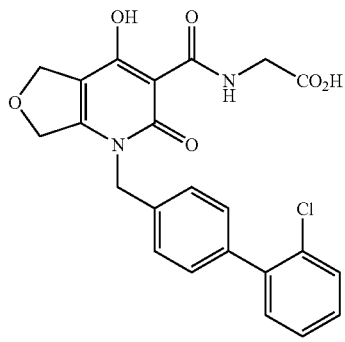

Step A Methyl 4-[(4-bromobenzyl)amino]-2,5-dihydrofuran-3-carboxylate (28-1)

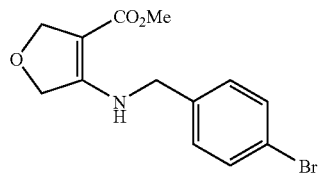

To a solution of methyl-4-oxo-tetrahydrofuro-3-carboxylate (1.0 g, 6.94 mmol) in ethanol (16 mL) was added 4-bromobenzylamine (1.621 g, 7.29 mmol) followed by triethylamine (0.919 mL, 6.59 mmol) and acetic acid (0.119 mL, 2.082 mmol). The mixture was refluxed for 2h. The mixture was concentrated in vacuo, taken up in EtOAc (30 mL) and water (30 mL). The organic layer was then washed with saturated NaHCO₃ (20 mL). The aqueous layer was then extracted with EtOAc (3×40 mL) and the combined organic extracts were washed with water (30 mL) and brine (30 mL), dried over Na₂SO₄ and concentrated in vacua to give a brown oil which solidified over time to an oily brown solid, which was taken on crude to the next reaction.

Step B Methyl-4-[(4-bromobenzyl)(3-ethoxy-3-oxopropanoyl)amino]-2,5-dihydrofuran-3-carboxylate (28-2)

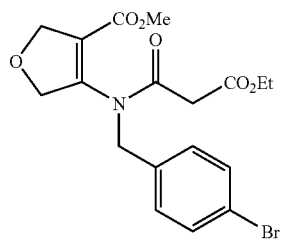

To a solution of the enamine from Step A (2.1 g, 6.73 mmol) in dichloromethane (50 ml) at 0° C. was added pyridine (0.816 ml, 10.09 mmol). Ethyl malonyl chloride (1.292 ml, 10.09 mmol) was then added dropwise followed by DMAP (0.164 g, 1345 mmol). The mixture was then warmed to room temperature and stirred for 2 H. A second charge of pyridine (0.816 mL), ethyl malonyl chloride (1.292 mL) and DMAP (164 mg) were added was added and the reaction stirred at ambient temperature for one hr. The mixture was concentrated in vacuo to give an orange oil, which was partitioned between EtOAc (30 mL) and water (30 mL). The layers were separated, and the aqueous layers were extracted with EtOAc (3×30 mL). The combined organic extracts were washed with 5% KHSO₄ (40 mL) and sat. NaHCO₃ (40 mL). The organic phase was then dried over MgSO₄, and concentrated in vacuo to give an orange oil which was taken on crude to the next reaction.

Step C Ethyl 1-(4-bromobenzyl)-4-hydroxy-2-oxo-1,2,5,7-tetrahydrofuro[3,4-b]pyridin-3-carboxylate (28-3)

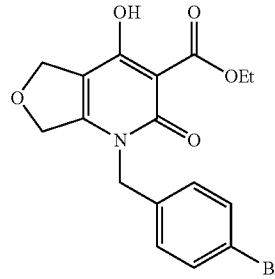

A solution of sodium ethoxide (0.671 g, 9.85 mmol) in ethanol (50 ml) was added to the N-acylated enamine from Step B (2.8 g, 6.57 mmol). This reaction mixture was heated in a sealed vial at 85° C. for 4 h. The reaction mixture was concentrated in vacuo to give a maroon oil. To this oil was added sat. NaH₂PO₄ (50 mL) and EtOAc (50 mL) and the layers were separated. The aqueous layer was then extracted with EtOAc (3×40 mL). The combined organic extracts were washed with water (40 mL), brine (40 mL), dried over MgSO₄, and concentrated in vacuo to give a yellow oil. The oil was taken up in dichloromethane, Et₂O and hexanes and concentrated several times until a solid formed. The solid was triturated with Et₂O and filtered to give compound 28-3 as a tan solid, 563 mg: ¹H NMR (500 MHz, CDCl₃): δ 1.45 (t, 3 H, J=7.1 Hz), 4.46 (q, 2 H, J=7.1 Hz), 4.89 (t, 2 H, J=3.0 Hz), 4.98 (s, 2 H), 5.03 (t, 2 H, J=3.2 Hz), 7.10 (d, 2 H, J=8.5 Hz), 7.45 (d, 2 H, J=8.5 Hz); HPLC/MS: 1.17 min, 395.0 (M+H)⁺.

Step D tort-butyl N-{[1-(4-bromobenzyl)-4-hydroxy-2-oxo-1,2,5,7-tetrahydrofuro[3,4-b]pyridin-3-yl]carbonyl}glycinate (28-4)

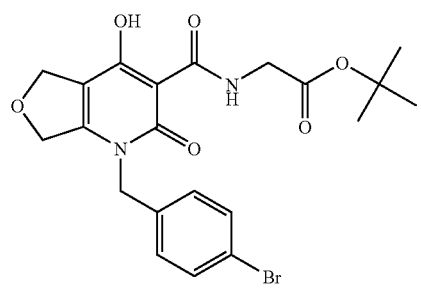

To a solution of the ester from Step C (563 mg, 1.43 mmol) in 1,2-dimethoxyethane (12 mL) was added tert-butyl glycine (0.390 mL, 2.86 mmol). The mixture was heated in the microwave at 120° C. for 1.5 h. The mixture was concentrated in vacuo to give a yellow oil which was taken up in the minimum amount of $CH_2Cl_2$ and chromatographed on a Biotage 40S+ column with a 10, 20, 30, EtOAc/hexanes gradient elution to give compound, 28-4, as a white solid, 494 mg: $^1H$ NMR (500 MHz, $CDCl_3$): δ 1.49 (s, 9 H), 4.09 (d, 2 H, J=5.2 Hz), 4.91 (t, 2 H, J=3.2 Hz), 5.01 (s, 2 H), 5.05 (t, 2 H, J=3.2 Hz), 7.09 (d, 2 H, 8.3 Hz), 7.46 (d, 2 H, J=8.2 Hz), 10.44 (m, 1 H); HPLC/MS: 1.28 min, 480.0 $(M+H)^+$.

Step E tert-butyl N-({1-[2'-chlorophenyl-4-yl)methyl]-4-hydroxy-2-oxo-1,2,5,7-tetrahydrofuro[3,4-b]pyridin-3-yl}carbonyl)glycinate (28-5)

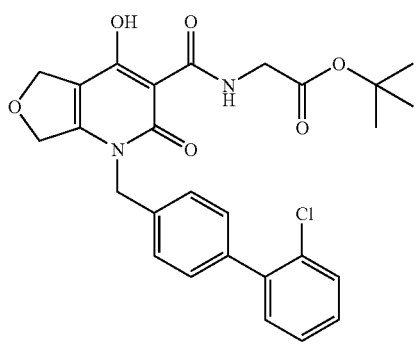

The aryl bromide from Step D {75 mg, 0.156 mmol) and 2-chlorophenylboronic acid (48.9 mg, 0.313 mmol) were added to a microwave vial followed by DMF (1.7 ml), ethanol (0.4 ml), and water (0.15 ml). Once mixed together, sodium carbonate (49.8 mg, 0.469 mmol) and palladium tetrakistriphenylphosphine (9.04 mg, 7.82 μmol) was added. The mixture was heated in the microwave at 120° C. for 45 min. The mixture was quenched with 5% aqueous $KHSO_4$ (10 mL) and extracted with EtOAc (3×10 mL). The combined organic extracts were washed with sat. $NaHCO_3$ (10 mL) followed by water (10 mL) and brine (10 mL). The organic extracts were then dried over $Na_2SO_4$ and concentrated in vacua to give a blackish oil which was taken up in the minimum amount of $CH_2Cl_2$ and chromatographed on a Biotage 25S+ column with a 10-20% acetone/hexanes gradient elution to give compound, 28-5, as a clear oil, 63 mg: $^1H$ NMR (500 MHz, $CDCl_3$): δ 1.49 (s, 9H), 4.09 (d, 2 H, J=5.5 Hz), 4.99 (t, 2 H, J=3.2 Hz), 5.07 (t, 2 H, J=2.9 Hz), 5.12 (s, 2 H), 7.26 (in, 6 H), 7.41 (in, 2 H). 10.50 (m, 1 H); HPLC/MS: 1.34 min, 511.0 $(M+H)^+$.

Step F N-({1-[2'-chlorophenyl-4-yl)methyl]-4-hydroxy-2-oxo-1,2,5,7-tetrahydrofuro[3,4-b]pyridin-3-yl}carbonyl)glycine (28-6)

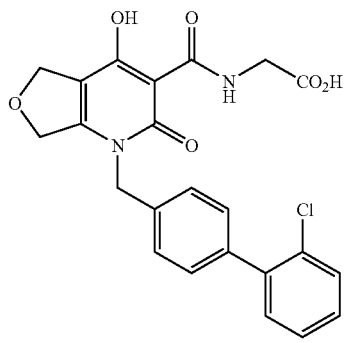

To solution of the tert-butyl ester from Step E (63 mg, 0.123 mmol) in dichloromethane (1.0 mL) at room temperature was added TFA (1.0 mL, 12.98 mmol). The reaction mixture was stirred at room temperature overnight. The reaction was concentrated in vacuo to give a yellow oil. The oil was then azeotroped with 1,2 dichloroethane to give an off-white solid which was triturated with $Et_2O$ to give compound, 28-6, as a light tan solid, 25 mg: $^1H$ NMR (500 MHz, DMSO-$d_6$): δ 4.07 (d, 2 H, J=5.7 Hz), 4.97 (m, 2 H), 5.06 (m, 2 H), 5.12 (s, 2 H), 7.32 (d, 2 H, J=8.2 Hz), 7.40 (m, 5 H) 7.55 (m, 1 H), 10.29 (t, 1 H, J=5.3 Hz), 12.85 (s, 1 H); HPLC/MS: 1.21 min, 455.0 $(M+H)^+$.

Example 29

N-[(1-{6-(2-chlorophenyl)pyridine-3-yl]methyl}-4-hydroxy-2-oxo-1,2,5,7-tetrahydrofuro[3,4-b]pyridin-3-yl}carbonyl)glycine (29-1)

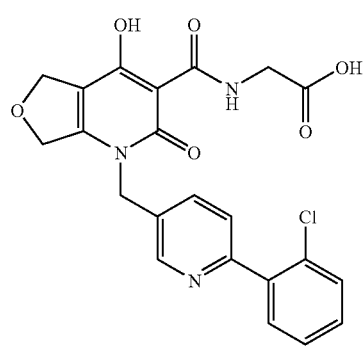

The title compound, 29-1, was prepared in a manner analogous to that described for EXAMPLE 28, substituting for 1-(6-chloropyridin-3-yl)methanamine for 4-bromobenzylamine hydrochloride in step A. $^1H$ NMR (500 MHz, DMSO-$d_6$): δ 4.06 (d, 2 H, J=5.5 Hz), 4.97 (s, 2 H), 5.13 (s, 4 H), 7.43-7.45 (in, 1 H), 7.55-7.64 (m, 1 H), 7.63 (d, 1 H, J=8.2 Hz), 7.75 (dd, 1 H, J=2.1, 8.2 Hz), 10.22 (t, 1 H J=5.5 Hz), 12.86 (br s, 1H); HPLC/MS; 2.80 min; 456.2 $(M+H)^+$.

Examples 30-54

The following compounds were prepared by using procedures analogous to those described for EXAMPLE 28, substituting an appropriately substituted amine for 4-bromobenylamine hydrochloride respectively, as outlined in Step A.

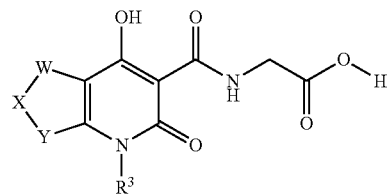

| EX-AMPLE | W | X | Y | R₃ | HPLC A/B (min) | MS m/z (M + H) |
|---|---|---|---|---|---|---|
| 30 | CH₂ | O | CH₂ | 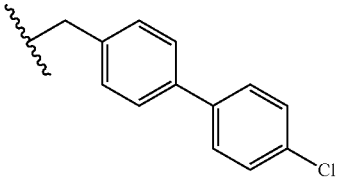 [SMILES: *Cc1ccc(-c2ccc(Cl)cc2)cc1] | 1.23 A | 455.1 |

N-({1-[4'-chlorophenyl)methyl]-4-hydroxy-2-oxo-1,2,5,7-tetrahydrofuro[3,4,-b]pyridin-3-yl}carbonyl)glycine
¹H NMR (500 MHz, DMSO-d₆): δ 4.07 (d, 2 H, J = 5.4 Hz), 4.95 (m, 2 H), 5.03 (m, 2 H), 5.11 (s, 2 H), 7.32 (d, 2 H, J = 8.2 Hz,), 7.5 (d, 2 H, J = 8.6 Hz), 7.65 (m, 4 H), 10.29 (t, 1 H, J = 5.5 Hz), 12.8 (s, 1H).

| 31 | CH₂ | O | CH₂ | 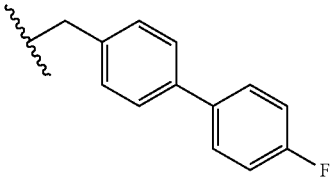 [SMILES: *Cc1ccc(-c2ccc(F)cc2)cc1] | 1.21 A | 439.1 |
|---|---|---|---|---|---|---|

N-({1-[4'-fluorophenyl)methyl]-4-hydroxy-2-oxo-1,2,5,7-tetrahydrofuro[3,4,-b]pyridin-3-yl}carbonyl)glycine
¹H NMR (500 MHz, DMSO-d₆): δ 4.06 (d, 2 H, J = 5.7 Hz), 4.95 (m, 2 H), 5.03 (m, 2 H), 5.09 (s, 2 H), 7.28 (m, 4 H), 7.60 (d, 2 H, J = 8.2 Hz), 7.65 (m, 2 H), 10.28 (t, 1 H, J = 5.5 Hz), 12.86 (s, 1 H).

| 32 | CH₂ | O | CH₂ | 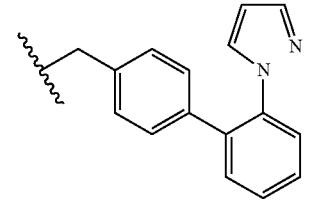 [SMILES: *Cc1ccc(-c2ccccc2N/C=C\C=N)cc1] | 1.14 A | 487.0 |
|---|---|---|---|---|---|---|

N-[(4-hydroxy-2-oxo-1-{[2'-(1H-pyrazol-yl)biphenyl-4-yl]methyl}-1,2,5,7-tetrahydrofuro[3,4-b]pyridin-3-yl}carbonyl)glycine
¹H NMR (500 MHz, DMSO-d₆): δ 4.06 (d, 2 H, J = 5.5 Hz), 4.95 (m, 4 H), 5.05 (s, 2 H), 6.28 (t, 1 H, J = 2.1 Hz), 7.01 (d, 2 H, J = 8.0 Hz), 7.13 (d, 2 H, 8.2 Hz), 7.52 (m, 5 H), 7.57 (m, 1 H), 10.27 (t, 1 H, J = 5.5 Hz), 12.86 (s, 1 H).

| 33 | CH₂ | O | CH₂ | 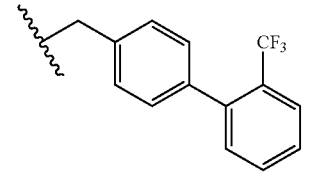 [SMILES: *Cc1ccc(-c2ccccc2C(F)(F)F)cc1] | 1.22 A | 489.1 |
|---|---|---|---|---|---|---|

N-[(4-hydroxy-2-oxo-1-{[2'-(trifluoromethyl)biphenyl-4-yl]methyl}-1,2,5,7-tetrahydrofuro[3,4-b]pyridin-3-yl}carbonyl)glycine
¹H NMR (500 MHz, DMSO-d₆): δ 4.07 (d, 2 H, J = 5.5 Hz), 4.97 (m, 2 H), 5.03 (m, 2 H), 5.13 (s, 2H), 7.29 (s, 4 H), 7.38 (d, 1 H, J = 7.5 Hz), 7.60 (t, 1 H, J = 7.7 Hz), 7.70 (t, 1 H, J = 7.6 Hz), 7.81 (d, 1 H, J = 7.8 Hz), 10.29 (t, 1 H, J = 5.5 Hz), 12.86 (s, 1 H).

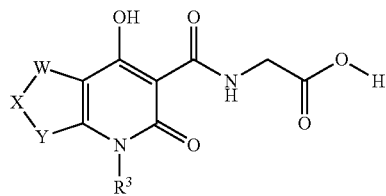

| EX-AMPLE | W | X | Y | R₃ | HPLC A/B (min) | MS m/z (M + H) |
|---|---|---|---|---|---|---|
| 34 | $CH_2$ | O | $CH_2$ | 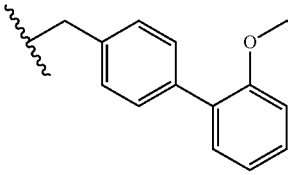 | 1.19 A | 519.0 |

N-[(4-hydroxy-1-{[2'-(2,2,2-trifluoroethoxy)biphenyl-4-yl]methyl}-2-oxo-1,2,5,7-tetrahydrofuro[3,4-b]pyridin-3-yl}carbonyl)glycine
¹H NMR (500 MHz, DMSO-d₆): δ 4.07 (d, 2 H, J = 5.5 Hz), 4.75 (q, 2 H, J = 8.9 Hz), 4.96 (m, 2 H), 5.04 (m, 2 H), 5.11 (s, 2 H), 7.11 (t, 1 H, J = 7.4 Hz), 7.20 (d, 1 H, J = 8.3 Hz), 7.28 (d, 2 H, J = 8.0 Hz), 7.34 (m, 2 H), 7.46 (d, 2 H, J = 8.2 Hz), 10.30 (t, 1 H, J = 5.5 Hz), 12.86 (s, 1 H).

| 35 | $CH_2$ | O | $CH_2$ | 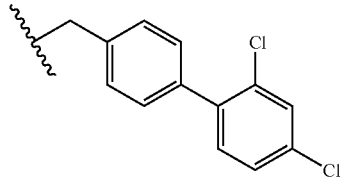 [SMILES: *Cc1ccc(-c2ccc(Cl)cc2Cl)cc1] | 1.26 A | 490.0 |

N-({1-[2',4'-dichlorobiphenyl-4-yl)methyl]-4-hydroxy-2-oxo-1,2,5,7-tetrahydrofuro[3,4-b]pyridin-3-yl}carbonyl)glycine
¹H NMR (500 MHz, DMSO-d₆): δ 4.06 (d, 2 H, J = 5.5 Hz), 4.96 (m, 2 H), 5.05 (m, 2 H), 5.11 (s, 2 H), 7.32 (d, 2 H, J = 8.2 Hz), 7.40 (m, 3 H), 7.49 (m, 1 H), 7.71 (s, 1 H), 10.28 (t, 1 H, J = 5.5 Hz), 12.86 (s, 1 H).

| 36 | $CH_2$ | O | $CH_2$ | 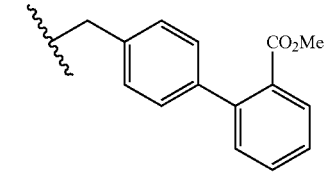 [SMILES: *Cc1ccc(-c2ccccc2C(=O)OC)cc1] | 1.17 A | 479.1 |

N-[(4-hydroxy-1-{[2'-(methoxycarbonyl)biphenyl-4-yl]methyl}-2-oxo-1,2,5,7-tetrahydrofuro[3,4,-b]pyridin-3-yl}carbonyl)glycine
¹H NMR (500 MHz, DMSO-d₆): δ 3.58 (s, 3 H), 4.07 (d, 2 H, J = 5.5 Hz), 4.96 (m, 2 H), 5.02 (m, 2 H), 5.12 (s, 2 H), 7.27 (m, 4 H), 7.41 (d, 1 H, J = 7.6 Hz), 7.47 (t, 1 H, J = 6.6 Hz), 7.60 (t, 1 H, J = 6.2 Hz), 7.23 (d, 1 H, J = 6.6 Hz), 10.30 (t, 1 H, J = 5.5 Hz), 12.87 (s, 1 H).

| 37 | $CH_2$ | O | $CH_2$ | 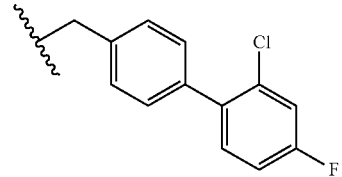 [SMILES: *Cc1ccc(-c2ccc(F)cc2Cl)cc1] | 1.41 A | 473.0 |

N-({1-[2'-chloro-4'-fluorobiphenyl-4-yl)methyl]-4-hydroxy-2-oxo-1,2,5,7-tetrahydrofuro[3,4-b]pyridin-3-yl}carbonyl)glycine
¹H NMR (500 MHz, DMSO-d₆): δ 4.07 (d, 2 H, J = 5.4 Hz), 4.97 (m, 2 H), 5.06 (m, 2 H), 5.12 (s, 2 H), 7.31 (m, 3 H), 7.39 (d, 2 H, J = 8.0 Hz), 7.45 (m, 1 H), 7.55 (m, 1 H), 10.28 (t, 1 H, J = 5.3 Hz), 12.84 (s, 1 H).

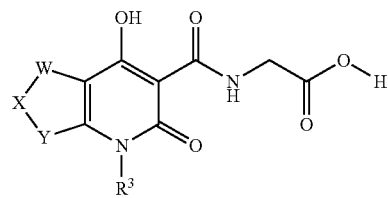

| EX-AMPLE | W | X | Y | R₃ | HPLC A/B (min) | MS m/z (M + H) |
|---|---|---|---|---|---|---|
| 38 | CH₂ | O | CH₂ | 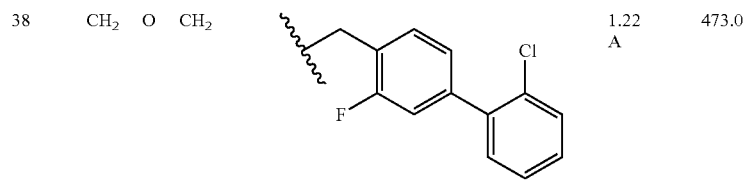 | 1.22 A | 473.0 |

N-({1-[2'-chloro-3-fluorobiphenyl-4-yl)methyl]-4-hydroxy-2-oxo-1,2,5,7-tetrahydrofuro[3,4-b]pyridin-3-yl}carbonyl)glycine
¹H NMR (500 MHz, DMSO-d₆): δ 4.05 (d, 2 H, J = 5.7 Hz), 4.99 (m, 2 H), 5.09 (m, 2 H), 5.12 (s, 2 H), 7.22 (m, 2 H), 7.32 (d, 1 H, J = 10.3 Hz), 7.42 (m, 3 H), 7.56 (m, 1 H), 10.19 (t, 1 H, 5.8 Hz), 12.81 (s, 1 H).

| 39 | CH₂ | O | CH₂ | 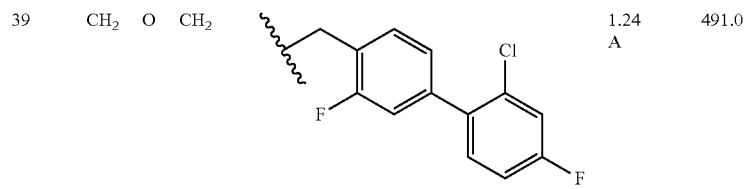 | 1.24 A | 491.0 |

N-({1-[2'-chloro-3,4'-difluorobiphenyl-4-yl)methyl]-4-hydroxy-2-oxo-1,2,5,7-tetrahydrofuro[3,4-b]pyridin-3-yl}carbonyl)glycine
¹H NMR (500 MHz, DMSO-d₆): δ 4.04 (d, 2 H, J = 5.4 Hz), 4.99 (m, 2 H), 5.09 (m, 2 H), 5.11 (s, 2 H), 7.21 (m, 2 H), 7.31 (m, 2 H), 7.48 (m, 1 H), 7.57 (m, 1 H), 10.18 (t, 1 H, J = 5.7 Hz), 12.34 (s, 1 H).

| 40 | CH₂ | O | CH₂ | 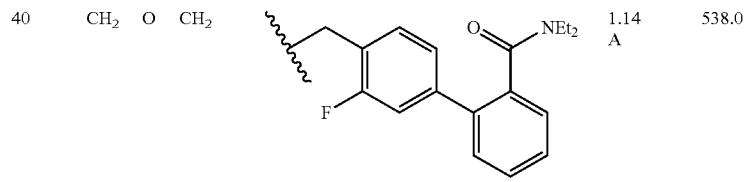 | 1.14 A | 538.0 |

N-{[1-({2'-(diethylamino)carbonyl]-3-fluorobiphenyl-4-yl}methyl)-4-hydroxy-2-oxo-1,2,5,7-tetrahydrofuro[3,4-b]pyridin-3-yl}carbonyl)glycine
¹H NMR (500 MHz, DMSO-d₆): δ 0.74 (t, 3 H, J = 7.1 Hz), 0.79 (t, 3 H, J = 7.1 Hz), 2.84 (m, 3 H), 3.61 (m, 1 H), 4.05 (d, 2 H, J = 5.5 Hz), 4.97 (m, 2 H), 5.03 (m, 2 H), 5.11 (s, 2 H), 7.20 (m, 3 H), 7.31 (m, 1 H), 7.46 (m, 3 H), 10.19 (t, 1 H, J = 5.5 Hz), 12.83 (s, 1 H).

| 41 | CH₂ | O | CH₂ | 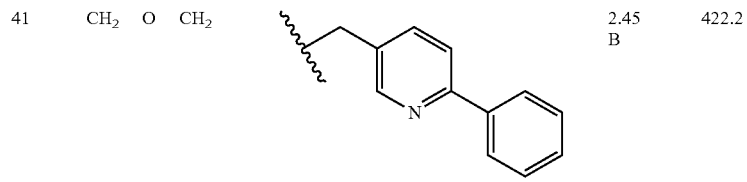 | 2.45 B | 422.2 |

N-({4-hydroxy-2-oxo-1-[(6-phenylpyridin-3-yl)methyl]-1,2,5,7-tetrahydrofuro[3,4-b]pyridin-3-yl}carbonyl)glycine
¹H NMR (500 MHz, DMSO-d₆): δ 4.06 (d, 2 H, J = 5.5 Hz), 4.96 (s, 2 H), 5.10-5.12 (m, 4 H), 7.43-7.49 (m, 3 H), 7.55-7.64 (m, 1 H), 7.72-7.76 (m, 1 H), 7.92 (d, 1 H, J = 7.3 Hz), 8.03 (d, 1 H, J = 7.5 Hz), 10.16 (t, 1 H, J = 5.5 Hz), 12.81 (br s, 1 H).

-continued

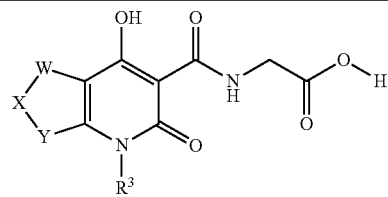

| EXAMPLE | W | X | Y | R₃ | HPLC A/B (min) | MS m/z (M + H) |
|---|---|---|---|---|---|---|
| 42 | CH₂ | O | CH₂ | 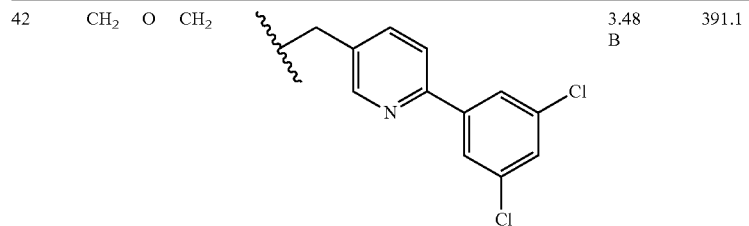 | 3.48 B | 391.1 |

N-[(1-{[6-(3,5-dichlorophenyl)pyridin-3-yl]methyl}-4-hydroxy-2-oxo-1,2,5,7-tetrahydrofuro[3,4-b]pyridin-3-yl)carbonyl]glycine
$^1$H NMR (500 MHz, DMSO-d$_6$): δ 4.06 (d, 2 H, J = 5.5 Hz), 4.96 (s, 2 H), 5.11 (s, 4 H), 7.65 (s, 1 H), 7.78 (d, 1 H, J = 8.3 Hz), 8.04 (d, 1 H, J = 8.3 Hz), 8.07 (d, 1 H, J = 1.4 Hz), 8.42 (s, 1 H), 10.21 (t, 1 H, J = 5.5 Hz), 12.81 (br s, 1 H).

| 43 | CH₂ | O | CH₂ | 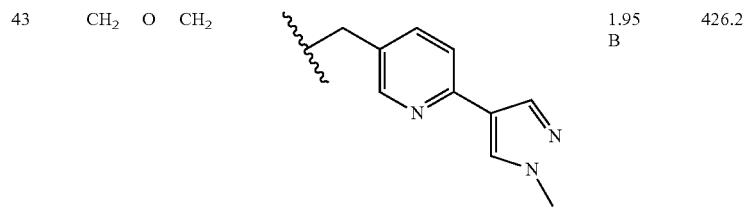 | 1.95 B | 426.2 |
|---|---|---|---|---|---|---|

N-[(4-hydroxy-1-{[6-(1-methyl-1H-pyrazol-4-yl)pyridin-3-yl]methyl}-2-oxo-1,2,5,7-tetrahydrofuro[3,4-b]pyridin-3-yl)carbonyl]glycine
$^1$H NMR (500 MHz, DMSO-d$_6$): δ 3.87 (s, 3 H), 4.06 (d, 2 H, J = 5.5 Hz), 4.94 (s, 2 H), 5.04 (s, 2 H), 5.10 (s, 2 H), 7.62 (d, 1 H, J = 8.0 Hz), 7.67 (d, 1 H, J = 1.7, 8.1 Hz), 7.97 (s, 1 H), 8.27 (s, 1 H), 8.47 (d, 1 H, J = 1.6 Hz), 10.23 (t, 1 H, J = 5.5 Hz), 12.81 (br s, 1 H).

| 44 | CH₂ | O | CH₂ | 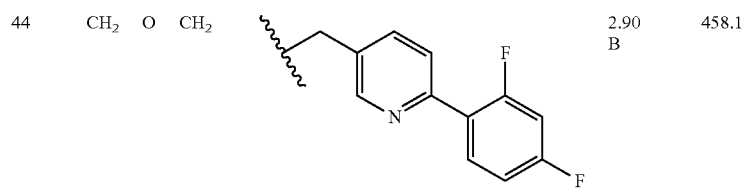 | 2.90 B | 458.1 |
|---|---|---|---|---|---|---|

N-[(1-{[6-(2,4-difluorophenyl)pyridin-3-yl]methyl}-4-hydroxy-2-oxo-1,2,5,7-tetrahydrofuro[3,4-b]pyridin-3-yl)carbonyl]glycine
$^1$H NMR (500 MHz, DMSO-d$_6$): δ 4.06 (d, 2 H, J = 5.5 Hz), 4.96 (s, 2 H), 5.11-5.12 (m, 4 H), 7.20-7.24 (m, 1 H), 7.35-7.40 (m, 1 H), 7.72-7.77 (m, 2 H), 7.95-7.97 (m, 1 H), 8.67 (d, 1 H, J = 1.6 Hz), 10.21 (t, 1 H, J = 5.5 Hz), 12.81 (br s, 1 H).

| 45 | CH₂ | O | CH₂ | 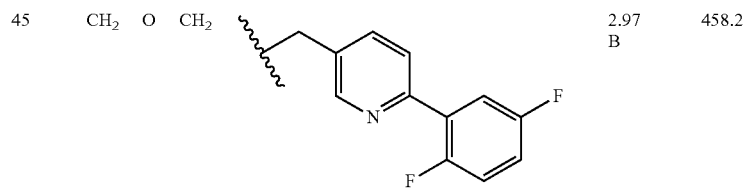 | 2.97 B | 458.2 |
|---|---|---|---|---|---|---|

N-[(1-{[6-(2,5-difluorophenyl)pyridin-3-yl]methyl}-4-hydroxy-2-oxo-1,2,5,7-tetrahydrofuro[3,4-b]pyridin-3-yl)carbonyl]glycine
$^1$H NMR (500 MHz, DMSO-d$_6$): δ 4.06 (d, 2 H, J = 5.5 Hz), 4.97 (s, 2 H), 5.12 (m, 4 H), 7.33-7.40 (m, 2 H), 7.70-7.79 (m, 3 H), 8.67 (d, 1 H, J = 1.6 Hz), 10.21 (t, 1 H, J = 5.5 Hz), 12.81 (br s, 1 H).

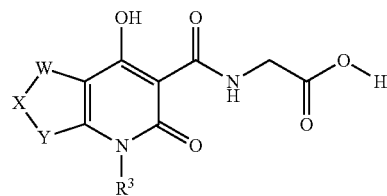

| EX-AMPLE | W | X | Y | R₃ | HPLC A/B (min) | MS m/z (M + H) |
|---|---|---|---|---|---|---|
| 46 | CH₂ | O | CH₂ | 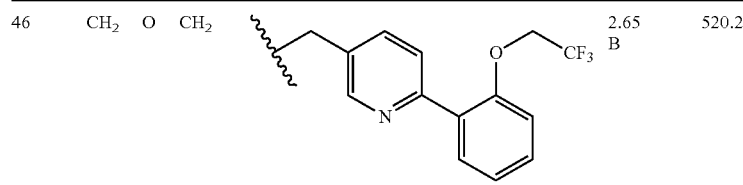 | 2.65 B | 520.2 |

N-{[4-hydroxy-2-oxo-1-({6-[2,2,2-trifluoroethoxy)phenyl]pyridin-3-yl}methyl]-1,2,5,7-tetrahydrofuro[3,4-b]pyridin-3-yl]carbonyl}glycine
$^1$H NMR (500 MHz, DMSO-d$_6$): δ 4.06 (d, 2 H, J = 5.5 Hz), 4.85 (q, 2 H, J = 8.9 Hz), 4.97 (s, 2 H), 5.12 (m, 4 H), 7.17 (t, 1 H, J = 7.5 Hz), 7.25 (d, 1 H, J = 8.3 Hz), 7.45 (t, 1 H, J = 8.3 Hz), 7.75 (dd, 1 H, J = 1.7, 7.6 Hz) 7.83 (s, 1 H), 8.67 (s, 1 H), 10.22 (t, 1 H, J = 5.5 Hz), 12.81 (br s, 1 H).

| 47 | CH₂ | O | CH₂ | 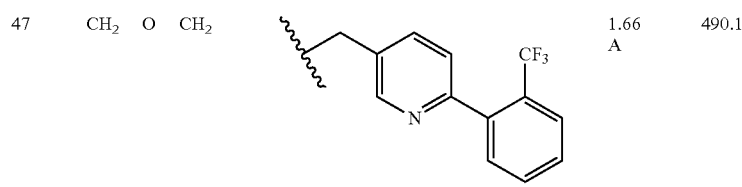 | 1.66 A | 490.1 |
|---|---|---|---|---|---|---|

N-{[4-hydroxy-2-oxo-1-({6-[2-(trifluoromethyl)phenyl]pyridin-3-yl}methyl)-1,2,5,7-tetrahydrofuro[3,4-b]pyridin-3-yl]carbonyl}glycine
$^1$H NMR (500 MHz, DMSO-d$_6$): δ 4.06 (d, 2 H, J = 5.5 Hz), 4.97 (s, 2 H), 5.11 (m, 2 H), 5.14 (m, 2 H), 7.46-7.82 (m, 6 H), 8.62 (d, 1 H, J = 1.9 Hz), 10.23 (t, 1 H, J = 5.5 Hz), 12.84 (br s, 1 H).

| 48 | CH₂ | O | CH₂ | 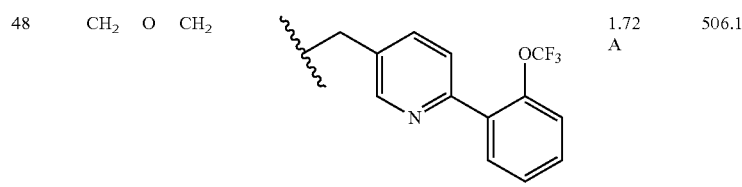 | 1.72 A | 506.1 |
|---|---|---|---|---|---|---|

N-{[4-hydroxy-2-oxo-1-({6-[2-(trifluoromethoxy)phenyl]pyridin-3-yl}methyl)-1,2,5,7-tetrahydrofuro[3,4-b]pyridin-3-yl]carbonyl}glycine
$^1$H NMR (500 MHz, DMSO-d$_6$): δ 4.06 (d, 2 H, J = 5.5 Hz), 4.97 (s, 2 H), 5.12 (m, 4 H), 7.46-7.82 (m, 6 H), 8.67 (s, 1 H), 10.22 (t, 1 H, J = 5.5 Hz), 12.83 (br s, 1 H).

| 49 | CH₂ | O | CH₂ | 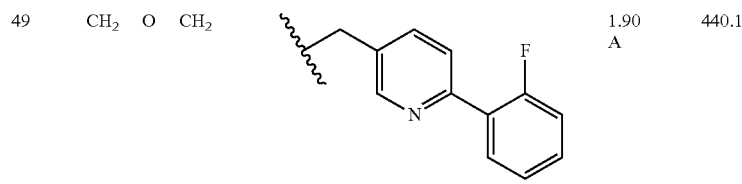 | 1.90 A | 440.1 |
|---|---|---|---|---|---|---|

N-[(1-{[6-(2-fluorophenyl)pyridin-3-yl]methyl}-4-hydroxy-2-oxo-1,2,5,7-tetrahydrofuro[3,4-b]pyridin-3-yl)carbonyl]glycine
$^1$H NMR (500 MHz, DMSO-d$_6$): δ 4.06 (d, 2 H, J = 5.5 Hz), 4.97 (s, 2 H), 5.12 (m, 4 H), 7.29-7.33 (m, 2 H), 7.45-7.50 (m, 1 H), 7.75 (s, 2 H), 7.87-7.91 (m, 1 H), 8.67 (s, 1 H), 10.22 (t, 1 H, J = 5.5 Hz), 12.81 (br s, 1 H).

-continued

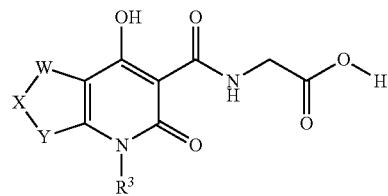

| EX-AMPLE | W | X | Y | R₃ | HPLC A/B (min) | MS m/z (M + H) |
|---|---|---|---|---|---|---|
| 50 | CH₂ | O | CH₂ | 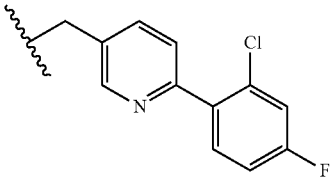 [SMILES: *Cc1ccc(-c2ccc(F)cc2Cl)nc1] | 1.64 A | 474.1 |

N-[(1-{[6-(2-chloro-4-fluorophenyl)pyridin-3-yl]methyl}-4-hydroxy-2-oxo-1,2,5,7-tetrahydrofuro[3,4-b]pyridin-3-yl)carbonyl]glycine
¹H NMR (500 MHz, DMSO-d₆): δ 4.06 (d, 2 H, J = 5.5 Hz), 4.97 (s, 2 H), 5.12 (m, 4 H), 7.33 (ddd, 1 H, J = 2.7, 8.4, 8.5 Hz), 7.56 (dd, 1 H, J = 2.5, 8.9 Hz), 7.57-7.64 (m, 2 H), 7.76 (dd, 1 H, J = 2.3, 8.2 Hz), 8.65 (d, 1 H, J = 1.8 Hz), 10.22 (t, 1 H, J = 5.5 Hz), 12.83 (br s, 1 H).

| 51 | CH₂ | O | CH₂ | 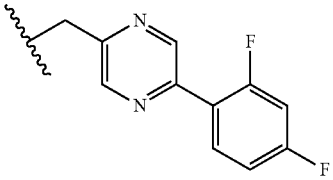 [SMILES: *Cc1cnc(-c2ccc(F)cc2F)cn1] | 2.90 B | 459.2 |

N-[(1-{[5-(2,4-difluorophenyl)pyrazin-2-yl]methyl}-4-hydroxy-2-oxo-1,2,5,7-tetrahydrofuro[3,4-b]pyridin-3-yl)carbonyl]glycine
¹H NMR (500 MHz, DMSO-d₆): δ 4.06 (d, 2 H, J = 5.5 Hz), 5.00 (s, 2 H), 5.17 (s, 2 H), 5.22 (s, 2 H), 7.26-7.30 (m, 1 H), 7.42-7.48 (m, 1 H), 7.95-8.00 (m, 1 H), 8.89 (s, 1 H), 8.91 (s, 1 H), 10.12 (t, 1 H, J = 5.5 Hz), 12.82 (br s, 1 H).

| 52 | CH₂ | O | CH₂ | 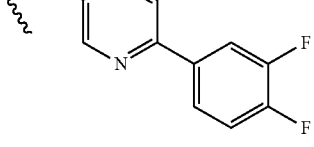 | 2.90 B | 459.2 |

N-[(1-{[5-(3,4-difluorophenyl)pyrazin-2-yl]methyl}-4-hydroxy-2-oxo-1,2,5,7-tetrahydrofuro[3,4-b]pyridin-3-yl)carbonyl]glycine
¹H NMR (500 MHz, DMSO-d₆): δ 4.06 (d, 2 H, J = 5.5 Hz), 5.01 (s, 2 H), 5.17 (s, 2 H), 5.21 (s, 2 H), 7.57-7.62 (m, 1 H), 7.97-7.99 (m, 1 H), 8.13-8.17 (m, 1 H), 8.83 (s, 1 H), 9.18 (s, 1 H), 10.12 (t, 1 H, J = 5.5 Hz), 12.81 (br s, 1 H).

| 53 | CH₂ | O | CH₂ | 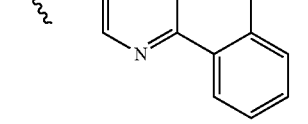 | 3.06 B | 457.1 |

N-[(1-{[5-(2-chlorophenyl)pyrazin-2-yl]methyl}-4-hydroxy-2-oxo-1,2,5,7-tetrahydrofuro[3,4-b]pyridin-3-yl)carbonyl]glycine
¹H NMR (500 MHz, DMSO-d₆): δ 4.02 (d, 2 H, J = 5.5 Hz), 5.01 (s, 2 H), 5.17 (s, 2 H), 5.23 (s, 2 H), 7.49-7.52 (m, 2 H), 7.60-7.64 (m, 2 H), 8.85 (s, 1 H), 8.89 (s, 1 H), 10.13 (t, 1 H, J = 5.5 Hz), 12.82 (br s, 1 H).

-continued

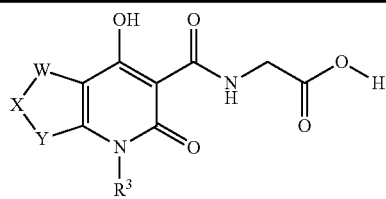

| EX-AMPLE | W | X | Y | R₃ | HPLC A/B (min) | MS m/z (M + H) |
|---|---|---|---|---|---|---|
| 54 | CH₂ | O | CH₂ | (pyrazinylmethyl with 2-trifluoromethoxyphenyl) | 3.24 B | 507.2 |

N-[(1-{[5-(2-trifluoromethoxyphenyl)pyrazin-2-yl]methyl}-4-hydroxy-2-oxo-1,2,5,7-tetrahydrofuro[3,4-b]pyridin-3-yl)carbonyl]glycine
$^1$H NMR (500 MHz, DMSO-d$_6$): δ 4.06 (d, 2 H, J = 5.5 Hz), 5.01 (s, 2 H), 5.16 (s, 2 H), 5.23 (s, 2 H), 7.53-7.57 (m, 2 H), 7.62-7.66 (m, 1 H), 7.81-7.83 (m, 1 H), 8.85 (s, 1 H), 8.90 (s, 1 H), 10.13 (t, 1 H, J = 5.5 Hz), 12.82 (br s, 1 H).

Biological Assays

The exemplified compounds, Examples 1 through 54, of the present invention, have been found to inhibit the interaction between PHD2 and HIF and exhibit IC$_{50}$ values ranging between 1 nanomolar to 10 micromolar. Non-limiting examples of assays that may be useful to detect favorable activity are disclosed in the following publications: Oehme, F., et al., *Anal. Biochem.* 330:74-80 (2004); Hirsilä, M, et al., *J. Bio. Chem.* 278 (33): 30772-30780 (2005); Hyunju, C., et al., *Biochem. Biophys. Res. Comm.* 330 (2005) 275-280; and Hewitson, K. S., et al., *Methods in Enzymology*, (Oxygen Biology and Hypoxia); Elsevier Publisher (2007), pg. 25-42 (ISSN: 0076-6879).

The biological activity of the present compounds may be evaluated using assays described herein below.
Assay for HIF-PHD2 Catalytic Activity To each well of a 96-well plate was added 1 μL of test compound in DMSO and 20 μl of assay buffer (50 mM Tris pH 7.4/0.01% Tween-20/0.1 mg/ml bovine serum albumin/10 μM ferrous sulfate/1mM sodium ascorbate/20 μg/ml catalase) containing 0.15 μg/ml FLAG-tagged full length PHD2 expressed in and purified from baculovirus-infected Sf9 cells. After a 30 min preincubation at room temperature, the enzymatic reactions were initiated by the addition of 4 μL of substrates (final concentrations of 0.2 μM 2-oxoglutarate and 0.5 μM HIF-1α peptide biotinyl-DLDLEMLAPYJPMDDDFQL). After 2 Hr at room temperature, the reactions were terminated and signals were developed by the addition of a 25 μL quench/detection mix to a final concentration of 1 mM ortho-phenanthroline, 0.1 mM EDTA, 0.5 nM anti-(His)$_6$ LANCE reagent (Perkin-Elmer Life Sciences), 100 nM AF647-labeled streptavidin (Invitrogen), and 2μg/ml (His)$_6$-VHL complex (S. Tan (2001) Protein Expr. Purif. 21, 224-234). The ratio of time resolved fluorescence signals at 665 and 620 nm was determined, and percent inhibition was calculated relative to an uninhibited control sample run in parallel.

Inhibition of the catalytic activity of HIF-PHD1 and HIF-PHD3 can be determined similarly.

The following Table entitled "PHD2 Binding Activity" includes the PHD2 binding activity for Examples 1-54 expressed as IC$_{50}$ (nM).

PHD2 Binding Activity

| EXAMPLE | PHD2 Binding Activity IC$_{50}$ (nM) |
|---|---|
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | ++ |
| 26 | + |
| 27 | + |
| 28 | + |
| 29 | + |
| 30 | + |
| 31 | + |
| 32 | + |
| 33 | + |
| 34 | + |
| 35 | + |
| 36 | + |
| 37 | + |
| 38 | + |
| 39 | + |
| 40 | + |
| 41 | + |
| 42 | + |

-continued

PHD2 Binding Activity

| EXAMPLE | PHD2 Binding Activity IC$_{50}$ (nM) |
|---|---|
| 43 | + |
| 44 | + |
| 45 | + |
| 46 | + |
| 47 | + |
| 48 | + |
| 49 | + |
| 50 | + |
| 51 | + |
| 52 | + |
| 53 | + |
| 54 | + |

+ = ≦10 IC$_{50}$ (nM)
++ = >10 to ≦100 IC$_{50}$ (nM)

What is claimed is:
1. A compound of formula I and pharmaceutically acceptable salts thereof

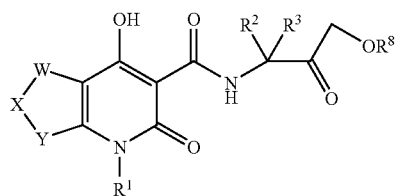

I wherein
one of X, Y, or W is O and the other two moieties are —CR$^4$R$^5$ and —CR$^6$R$^7$;
R$^8$ is selected from hydrogen, C$_{1-6}$ alkyl, optionally substituted with a hydroxy, —SH, —NH$_2$ or —CO$_2$H, and C$_{3-6}$ cycloalkyl optionally substituted with a hydroxy, —SH, —NH$_2$ or —CO$_2$H;
n is 0, 1, or 2;
R$^1$ is selected from
—C$_{1-10}$ alkyl,
—C$_{2-10}$ alkenyl,
—C$_{5-10}$ cycloalkenyl,
—C$_{2-10}$ alkynyl,
—C$_{0-10}$ alkylaryl,
—C$_{0-10}$ alkylheterocyclyl,
—C$_{0-10}$ alkyl-C$_{0-10}$cycloalkyl, and
perfluoroC$_{1-6}$alkyl;
wherein in R$^1$ said alkyl, alkenyl, alkynyl, cycloalkenyl, aryl, heterocycloalkyl, heterocyclyl, and cycloalkyl are each optionally substituted with one or more R$^9$ substituents;
R$^2$ and R$^3$ are independently selected from hydrogen, phenyl, heterocyclyl, and —C$_{1-10}$ alkyl,
wherein C$_{1-10}$ alkyl is unsubstituted or substituted with one or more fluorine atoms, and phenyl is unsubstituted or substituted with or more substituents selected from fluoro, chloro, hydroxyl,
C$_{1-10}$ alkyl, and —OC$_{1-10}$ alkyl;
R$^4$, R$^5$, R$^6$, and R$^7$ are independently selected from hydrogen, cyano, oxo, —C$_1$-C$_{10}$ alkyl, —C$_{2-10}$ alkenyl, C$_{3-10}$ cycloalkyl, —(C$_{1-10}$ alkyl)aryl, (C$_{0-10}$ alkyl)heterocyclyl, —C$_{5-10}$ cycloalkenyl, —C$_{2-10}$ alkynyl, —SO$_n$(C$_{1-10}$ alkyl) and —SO$_n$aryl wherein said alkyl, alkenyl, alkynyl, cycloalkyl, cycloalkenyl, aryl, and heterocyclyl are optionally substituted by one or more substituents R$^9$, and
optionally one set of substituents, R$^4$ and R$^5$, or R$^6$ and R$^7$, are linked together to form a ring of 5 to 8 atoms optionally substituted with one or more substituents R$^9$, where said ring is partially or fully unsaturated having 0, 1 or 2 heteroatoms independently selected from —NR$^6$—, —O— and —S(O)$_n$—;
R$^9$ is selected from halogen, hydroxy, oxo, cyano, aryl, heterocyclyl, —C$_{1-6}$ alkyl, O(C=O)$_{0-1}$C$_{1-6}$ alkyl, —C$_{1-6}$ alkoxy, —O$_{(0-1)}$(C$_{1-10}$)perfluoroalkyl, aryloxy, heterocyclyloxy, —CO$_2$R$^a$, —NR$^b$R$^c$, —CONR$^b$R$^c$, —OCO$_2$R$^a$, —OCONR$^b$R$^c$, —NR$^d$CO$_2$R$^a$, —NR$^d$CONR$^b$R$^c$, —SC$_{0-6}$ alkyl and —S(O)$_n$R$^d$, wherein said aryl, heterocyclyl, alkoxy, aryloxy, heterocyclyloxy are optionally substituted by one or more substituents R$^{10}$;
R$^{10}$ is selected from hydroxy, aryl, heterocyclyl, halogen, —C$_{1-6}$ alkyl, C$_{1-6}$ alkoxy, halogen, CO$_2$H, cyano, O(C=O)$_{0-1}$C$_{1-6}$ alkyl, NO$_2$, trifluoromethoxy, trifluoroethoxy, —O$_{(0-1)}$(C$_{1-10}$)perfluoroalkyl, C$_{0-10}$ alkylaminocarbonylamino, C$_{0-10}$ alkyloxycarbonylaminoC$_{0-10}$ alkyl, C$_{0-10}$ alkylcarbonylaminoC$_{0-10}$ alkyl, C$_{0-10}$ alkylaminosulfonylaminoC$_{0-10}$ alkyl, C$_{0-10}$ alkylsulfonylaminoC$_{0-10}$ alkyl, C$_{0-10}$ alkylsulfonyl, C$_{0-10}$ alkylaminosulfonyl, C$_{0-10}$alkylaminocarbonyl, —(C=O)N(C$_{0-6}$ alkyl)$_2$, —S(C$_{0-6}$ alkyl), and NH$_2$;
R$^a$ is chosen from hydrogen; —C$_{1-10}$ alkyl, —(C$_{1-6}$ alkyl)C$_{3-8}$ cycloalkyl; and
—(C$_{1-6}$ alkyl)phenyl; and
R$^b$, R$^c$, and R$^d$ are each independently chosen from hydrogen, —C$_{1-10}$ alkyl, —C$_{3-10}$ cycloalkyl, aryl, and heterocyclyl, wherein said alkyl, cycloalkyl, aryl and heterocyclyl are optionally substituted by one or more subtstituents R$^{10}$.

2. A compound of claim 1 wherein X is O, Y is —CR$^4$R$^5$ and W is —CR$^6$R$^7$.

3. A compound of claim 1 wherein Y is O, X is —CR$^4$R$^5$ and W is —CR$^6$R$^7$.

4. A compound of claim 1 wherein W is O, X is —CR$^4$R$^5$ and X is —CR$^6$R$^7$.

5. A compound of claim 1 wherein R$^1$ is selected from —C$_{0-10}$ alkylaryl, and —C$_{0-10}$ alkylheterocyclyl.

6. A compound of claim 1 wherein —C$_{0-10}$ alkylaryl is —C$_{1-3}$ alkylaryl and the aryl moiety is selected from phenyl, napthyl, tetrahydronaphthyl, indanyl, biphenyl and 2,3-dihydroindenyl.

7. A compound of claim 6 wherein the group —C$_{1-3}$ alkylaryl is selected from —C$_{1-3}$ alkyl phenyl, —C$_{1-3}$ alkyl biphenyl and —C$_{1-3}$ alkyl 2,3-dihydroindenyl.

8. A compound of claim 1 wherein —C$_{0-10}$ alkylheterocyclyl is —C$_{1-3}$ alkyl heterocyclyl and the heterocyclyl moiety is selected from azabenzimidazolyl, benzoimidazolyl, benzofuryl, benzofurazanyl, benzopyrazolyl, benzotriazolyl, benzothiophenyl, benzothiazolyl, benzothienyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazolinyl, isoxazolinyl, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, pyrimidinylphenyl, pyridinylphenyl, and benzo-1,3-dioxolyl.

9. A compound of claim 8, wherein —$C_{1-3}$ alkyl heterocyclyl and the heterocyclyl moiety is selected from indolyl, pyridinyl, phenyl, thiazolyl, triazolyl, oxadiazolyl, benzothiazolyl, oxazolyl, benzothienyl, pyrazolyl, pyrazinyl, pyridazinyl, and pyridinyl.

10. A compound of claim 5 wherein $R^8$ is hydrogen.

11. A compound of claim 1 selected from:
N-{[(1-(1,3-benzothiazol-2-ylmethyl)-4-hydroxy-2-oxo-1,2,5,7-tetrahydrofuro[3,4-b]pyridin-3-yl]carbonyl)glycine;
N-({4-hydroxy-2-oxo-1-[4-(trifluoromethyl)benzyl]-1,2,5, 7-tetrahydrofuro[3,4-b]pyridin-3-yl}carbonyl)glycine;
N-[(4-hydroxy-2-oxo-1-{[6-(trifluoromethyl)pyridine-3-yl]methyl}-1,2,5,7-tetrahydrofuro[3,4-b]pyridin-3-yl)carbonyl]glycine;
N-{[4-hydroxy-2-oxo-1-(pyridazin-3-ylmethyl)-1,2,5,7-tetrahydrofuro[3,4-b]pyridin-3-yl]carbonyl}glycine;
N-({4-hydroxy-2-oxo-1-[(5-phenyl-1,2,4-oxadiazol-3-yl)methyl]-1,2,5,7-tetrahydrofuro[3,4-b]pyridin-3-yl}carbonyl)glycine;
N-({4-hydroxy-2-oxo-1-[4-(trifluoromethoxy)benzyl]-1,2,5, 7-tetrahydrofuro[3,4-b]pyridin-3-y1}carbonyl)glycine;
N-({4-hydroxy-1-[(5-methylpyrazin-2-yl)methyl-2-oxo-1,2,5,7-tetrahydrofuro[3,4-b]pyridin-3-yl}carbonyl)glycine;
N-{[4-hydroxy-1-(4-isopropoxybenzyl)-2-oxo-1,2,5,7-tetrahydrofuro[3 4-b]pyridin-3-yl]carbonyl}glycine;
N-({1-[(6-chloropyridin-3-yl)methyl]-4-hydroxy-2-oxo-1,2,5,7-tetrahydrofuro[3,4-b]pyridin-3-yl}carbonyl)glycine;
N-{[1-(4-bromobenzyl)-4-hydroxy-2-oxo-1,2,5,7-tetrahydrofuro[3,4-b]pyridin-3-yl]carbonyl)glycine;
N-{[1-(2,3-dihydro-1H-inden-2-ylmethyl)-4-hydroxy-2-oxo-1,2,5,7-tetrahydrofuro[3,4-b]pyridin-3-yl]carbonyl}glycine;
N-({1-[(5-chloropyrazin-2-yl)methyl]-4-hydroxy-2-oxo-1,2,5,7-tetrahydrofuro[3,4-b]pyridin-3-yl}carbonyl)glycine;
N-({4-hydroxy-5-methyl-2-oxo-1-[4-(trifluoromethyl)benzyl]-1,2,5,7-tetrahydrofuro[3,4-b]pyridin-3-yl}carbonyl)glycine;
N-[(4-hydroxy-5-methyl-2-oxo-1-{[6-(trifluoromethyl)pyridine-3-yl]methyl}-1,2,5,7-tetrahydrofuro[3,4-b]pyridin-3-yl}carbonyl)glycine;
N-{[1-(4-bromo-2-fluorobenzyl)-4-hydroxy-2-oxo-1,2,5,7-tetrahydrofuro[3,4-b]pyridin-3-yl]carbonyl}glycine;
N-{[1-(3-chlorobenzyl)-4-hydroxy-2-oxo-1,2,5,7-tetrahydrofuro[3,4-b]pyridin-3-yl]carbonyl}glycine;
N-{[1-(4-difluoromethoxybenzyl)-4-hydroxy-2-oxo-1,2, 5,7-tetrahydrofuro[3,4-b]pyridin-3-yl]carbonyl}glycine;
N-({4-hydroxy-2-oxo-1-[3-(1 H-pyrazole-1-yl)benzyl]-1,2,5,7-tetrahydrofuro[3,4-b]pyridin-3-yl}carbonyl)glycine;
N-[(4-hydroxy-2-oxo-1-{[6-(2,2,2-trifluoroethoxy)pyridin-3-yl]methyl}-1,2,5,7-tetrahydrofuro[3,4-b]pyridin-3-yl)carbonyl]glycine;
N-[(4-hydroxy-1-{[1-(2-methylphenyl)-1H-pyrazol-3-yl]methyl}-2-oxo-1,2,5,7-tetrahydrofuro[3,4-b]pyridin-3-yl)carbonyl]glycine;
N-({4-hydroxy-1-[(5-methyl-2-phenyl-2H-1,2,3-triazol-4-yl)methyl]-2-oxo-1,2,5,7-tetrahydrofuro[3,4-b]pyridin-3-yl}carbonyl)glycine;
N-[(1-{[1-(4-fluorophenyl)-1 H-pyrazol-3-yl]methyl-4-hydroxy-2-oxo-1,2,5,7-tetrahydrofuro[3,4-b]pyridin-3-yl}carbonyl]glycine;
N-({4-hydroxy-2-oxo-1-[4-(1,3-thiazol-2-yl)benzyl]-1,2,5,7-tetrahydrofuro[3,4-b]pyridin-3-yl}carbonyl)glycine;
N-({4-hydroxy-2-oxo-1-[4-(2,2,2-trifluoroethoxy)benzyl]-1,2,5,7-tetrahydrofuro[3,4-b]pyridin-3-yl}carbonyl)glycine;
N-{[(1-(1,3-benzothiazol-2-ylmethyl)-4-hydroxy-7,7-dimethyl-2-oxo-1,2,5,7-tetrahydrofuro[3,4-b]pyridin-3-yl]carbonyl}glycine;
N-[(1-{[4-(2,4-dichlorophenyl)-1,3-thiazol-2-yl]methyl}-4-hydroxy-2-oxo-1,2,5,7-tetrahydrofuro[3,4-b]pyridin-3-yl]carbonyl]glycine;
N-[(1-{[4-(2-chlorophenyl)-1,3-thiazol-2-yl]methyl}-4-hydroxy-2-oxo-1,2,5,7-tetrahydrofuro[3,4-b]pyridin-3-yl]carbonyl]glycine;
N-({1-[2'-chlorobiphenyl)methyl]-4-hydroxy-2-oxo-1,2,5,7-tetrahydrofuro[3,4-b]pyridin-3-yl}carbonyl)glycine;
N-[(1-{[6-(2-chlorophenyl)pyridine-3-yl]methyl}-4-hydroxy-2-oxo-1,2,5,7-tetrahydrofuro[3,4-b]pyridin-3-yl]carbonyl)glycine;
N-({1-[4'-chlorophenyl)methyl]-4-hydroxy-2-oxo-1,2,5,7-tetrahydrofuro[3,4-b]pyridin-3-yl}carbonyl)glycine;
N-({1-[4'-fluorophenyl)methyl]-4-hydroxy-2-oxo-1,2,5,7-tetrahydrofuro[3,4-b]pyridin-3-yl}carbonyl)glycine;
N-[(4-hydroxy-2-oxo-1-{[2'-(1H-pyrazol-yl)biphenyl-4-yl]methyl}-1,2,5,7-tetrahydrofuro[3,4-b]pyridin-3-yl}carbonyl)glycine;
N-[(4-hydroxy-2-oxo-1-{[2'-(trifluoromethyl)biphenyl-4-yl]methyl}1,2,5,7-tetrahydrofuro[3,4-b]pyridin-3-yl}carbonyl)glycine;
N-[(4-hydroxy-1-{[2'-(2,2,2-trifluoroethoxy)biphenyl-4-yl]methyl}-2-oxo-1,2,5,7-tetrahydrofuro[3,4-b]pyridin-3-yl}carbonyl)glycine;
N-({1-[2',4'-dichlorobiphenyl-4-yl)methyl]-4-hydroxy-2-oxo-1,2,5,7-tetrahydrofuro[3,4-b]pyridin-3-yl}carbonyl)glycine;
N-[(4-hydroxy-1-{[2'-(methoxycarbonyl)biphenyl-4-yl]methyl}-2-oxo-1,2,5,7-tetrahydrofuro[3,4-b]pyridin-3-yl}carbonyl)glycine;
N-({1-[2'-chloro-4'-fluorobiphenyl-4-yl)methyl]-4-hydroxy-2-oxo-1,2,5,7-tetrahydrofuro[3,4-b]pyridin-3-yl}carbonyl)glycine;
N-({1-[2'-chloro-3-fluorobiphenyl-4-yl)methyl]-4-hydroxy-2-oxo-1,2,5,7-tetrahydrofuro[3,4-b]pyridin-3-yl}carbonyl)glycine;
N-({1-[2'-chloro-3,4'-difluorobiphenyl-4-yl)methyl]-4-hydroxy-2-oxo-1,2,5,7-tetrahydrofuro[3,4-b]pyridin-3-yl}carbonyl)glycine;
N-{[1-({2'-(diethylamino)carbonyl]-3-fluorobiphenyl-4-yl}methyl)-4-hydroxy-2-oxo-1,2,5,7-tetrahydrofuro[3,4-b]pyridin-3-yl}carbonyl)glycine;

N-({4-hydroxy-2-oxo-1-[(6-phenylpyridin-3-yl)methyl]
1,2,5,7-tetrahydrofuro[3,4-b]pyridin-3-yl}carbonyl)
glycine;

N-[(1-{[6-(3,5-dichlorophenyl)pyridin-3-yl]methyl}-4-
hydroxy-2-oxo-1,2,5,7-tetrahydrofuro[3,4-b]pyridin-3-
yl)carbonyl]glycine;

N-[(4-hydroxy-1-{[6-(1-methyl1H-pyrazol-4-yl)pyridin-
3-yl)methyl}-2-oxo-1,2,5,7-tetrahydrofuro[3,4-b]pyri-
din-3-yl)carbonyl]glycine;

N-[(1-{[6-(2,4-difluorophenyl)pyridin-3-yl]methyl}-4-
hydroxy-2-oxo-1,2,5,7-tetrahydrofuro[3,4-b]pyridin-3-
yl)carbonyl]glycine;

N-[(1-{[6-(2,5-difluorophenyl)pyridin-3-yl]methyl}-4-
hydroxy-2-oxo-1,2,5,7-tetrahydrofuro[3,4-b]pyridin-3-
yl)carbonyl]glycine;

N-{[4-hydroxy-2-oxo-1-({6-[2,2,2-trifluoroethoxy)phe-
nyl]pyridin-3-yl}methyl]1,2,5,7-tetrahydrofuro[3,4-b]
pyridin-3-yl]carbonyl}glycine;

N-{[4-hydroxy-2-oxo-1-({6-[2-(trifluoromethyl)phenyl]
pyridin-3-yl}methyl)-1,2,5,7-tetrahydrofuro[3,4-b]py-
ridin-3-yl]carbonyl}glycine;

N-{[4-hydroxy-2-oxo-1-({6-[2-(trifluoromethoxy)phe-
nyl]pyridin-3-yl}methyl)-1,2,5,7-tetrahydrofuro[3,4-b]
pyridin-3-yl]carbonyl}glycine;

N-[(1-{[6-(2-fluorophenyl)pyridin-3-yl]methyl}-4-hy-
droxy-2-oxo-1,2,5,7-tetrahydrofuro[3,4-b]pyridin-3-
yl)carbonyl]glycine;

N-[(1-{[6-(2-chloro-4-fluorophenyl)pyridin-3-yl]me-
thyl}-4-hydroxy-2-oxo-1,2,5,7-tetrahydrofuro[3,4-b]
pyridin-3-yl)carbonyl]glycine;

N-[(1-{[5-(2,4-difluorophenyl)pyrazin-2-yl]methyl}-4-
hydroxy-2-oxo-1,2,5,7-tetrahydrofuro[3,4-b]pyridin-3-
yl)carbonyl]glycine;

N-[(1-{[5-(3,4-difluorophenyl)pyrazin-2-yl]methyl}-4-
hydroxy-2-oxo-1,2,5,7-tetrahydrofuro[3,4-b]pyridin-3-
yl)carbonyl]glycine;

N-[(1-{[5-(2-chlorophenyl)pyrazin-2-yl]methyl}-4-hy-
droxy-2-oxo-1,2,5,7-tetrahydrofuro[3,4-b]pyridin-3-
yl)carbonyl]glycine;

N-[(1-{[5-(2-trifluoromethoxyphenyl)pyrazin-2-yl]me-
thyl}-4-hydroxy-2-oxo-1,2,5,7-tetrahydrofuro[3,4-b]
pyridin-3-yl)carbonyl]glycine, and pharmaceutically
acceptable salts thereof.

12. A pharmaceutical composition comprising a compound of claim 1 and pharmaceutically acceptable carrier.

13. A method of enhancing endogenous production of erythropoietin in a mammal which comprises administering to the mammal an amount of a compound of claim 1, or a pharmaceutically acceptable salt thereof that is effective for enhancing endogenous production of erythropoietin.

14. A method for treatment of anemia in a mammal which comprises administering to the mammal an effective amount of a compound of claim 1, or a pharmaceutically acceptable salt thereof.

* * * * *